United States Patent
Asami et al.

(10) Patent No.: US 9,158,382 B2
(45) Date of Patent: Oct. 13, 2015

(54) MEDICAL INFORMATION DISPLAY APPARATUS, METHOD, AND PROGRAM

(71) Applicant: FUJIFILM Corporation, Tokyo (JP)

(72) Inventors: Masahiro Asami, Tokyo (JP); Keigo Nakamura, Tokyo (JP); Hajime Shirasaka, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 13/780,840

(22) Filed: Feb. 28, 2013

(65) Prior Publication Data

US 2013/0179820 A1      Jul. 11, 2013

Related U.S. Application Data

(63) Continuation of application No. PCT/JP2011/004738, filed on Aug. 25, 2011.

(30) Foreign Application Priority Data

Aug. 31, 2010    (JP) .................................. 2010-194710

(51) Int. Cl.
*G06F 3/048* (2013.01)
*G06F 3/01* (2006.01)
(Continued)

(52) U.S. Cl.
CPC .............. *G06F 3/017* (2013.01); *A61B 1/0005* (2013.01); *A61B 1/00045* (2013.01);
(Continued)

(58) Field of Classification Search
CPC ........ G06F 3/017; G06Q 50/22; G06Q 50/24; G06Q 10/06; G06Q 10/10; A61B 1/00045; A61B 1/0004; A61B 1/00059
USPC .......................................................... 715/863
See application file for complete search history.

(56) References Cited

U.S. PATENT DOCUMENTS 6,747,672 B1 *   6/2004   Haakonsen et al. .......... 715/700
7,095,401 B2 *   8/2006   Liu et al. ...................... 345/156
(Continued)

FOREIGN PATENT DOCUMENTS

CN       101229048 A      7/2008
CN       103153171 A      6/2013
(Continued)

OTHER PUBLICATIONS

Karl-Hans Englmeier et al., "Gesture Analysis and Immersive Visualization for Virtual Endoscopy," 2001, Proceedings of SPIE vol. 4321, pp. 155-162.*
(Continued)

*Primary Examiner* — Doon Chow
*Assistant Examiner* — Andrew T Chiusano
(74) *Attorney, Agent, or Firm* — Young & Thompson

(57) ABSTRACT

The obtaining condition input user interface receives a gesture input while a subject appearance image (human body icon) is displayed, the endoscope condition identification unit recognizes an endoscope gesture representing an insertion path of an endoscope in the subject represented by the subject appearance image based on position information of the gesture and a position of the subject appearance image on the display surface and if, the endoscope gesture is recognized, identifies a medical information obtaining condition for obtaining medical information of an actual and/or a virtual endoscopic examination of the subject, the medical information obtaining unit selectively obtain medical information satisfying the identified medical information obtaining condition from the medical information database storing a plurality of sets of medical information, and the medical information display control unit displays the obtained medical information.

17 Claims, 28 Drawing Sheets

(51) Int. Cl.

| | | |
|---|---|---|
| *A61B 1/00* | (2006.01) | |
| *G06Q 10/06* | (2012.01) | |
| *G06Q 10/10* | (2012.01) | |
| *G06Q 50/22* | (2012.01) | |
| *A61B 1/04* | (2006.01) | |

(52) U.S. Cl.
CPC ........ *A61B 1/00048* (2013.01); *A61B 1/00059* (2013.01); *G06Q 10/06* (2013.01); *G06Q 10/10* (2013.01); *G06Q 50/22* (2013.01); *A61B 1/04* (2013.01)

(56) References Cited

U.S. PATENT DOCUMENTS

| | | | |
|---|---|---|---|
| 8,655,843 B2* | 2/2014 | Felt | 707/636 |
| 2001/0041992 A1* | 11/2001 | Lewis et al. | 705/3 |
| 2002/0118880 A1 | 8/2002 | Liu | |
| 2003/0018235 A1 | 1/2003 | Chen | |
| 2006/0195033 A1* | 8/2006 | Akimoto et al. | 600/429 |
| 2006/0251305 A1* | 11/2006 | Mohr | 382/128 |
| 2006/0281971 A1* | 12/2006 | Sauer et al. | 600/109 |
| 2006/0291709 A1* | 12/2006 | Haider | 382/128 |
| 2007/0076931 A1* | 4/2007 | Haider et al. | 382/128 |
| 2008/0114615 A1* | 5/2008 | Mahesh et al. | 705/2 |
| 2008/0267481 A1 | 10/2008 | Nakamura | |
| 2009/0138800 A1* | 5/2009 | Anderson et al. | 715/702 |
| 2010/0050110 A1* | 2/2010 | Hughes et al. | 715/781 |
| 2011/0289441 A1* | 11/2011 | Venon et al. | 715/771 |
| 2013/0174077 A1 | 7/2013 | Asami | |

FOREIGN PATENT DOCUMENTS

| | | |
|---|---|---|
| EP | 2612591 A1 | 7/2013 |
| JP | 8-083318 | 3/1996 |
| JP | 2005-080969 | 3/2005 |
| JP | 2005-304937 | 11/2005 |
| JP | 2006-198032 | 8/2006 |
| JP | 2007-323445 | 12/2007 |
| JP | 2008-259682 | 10/2008 |
| JP | 2009-119000 | 6/2009 |
| WO | 2004-052224 A1 | 6/2004 |
| WO | WO2012073119 A2 * | 6/2012 |

OTHER PUBLICATIONS

"Icon," Dictionary.com, retrieved Mar. 30, 2014, available at http://dictionary.reference.com/browse/icon?s=t.*
Extended European Search Report (EESR) dated May 27, 2014; Application No. 11821288.5.
Chinese Office Action dated Mar. 27, 2014; Publication No. 201180042127.4.
Chinese Office Action dated Nov. 15, 2014; Application Serial No. 20141110700680390.
European Office Action dated Jun. 2, 2015; U.S. Appl. No. 11 821 288.5.

* cited by examiner

FIG.7

| INFORMATION NO. | PATIENT ID | INDEX INFORMATION | | REAL DATA |
|---|---|---|---|---|
| | | GESTURE TYPE | GESTURE REGION | |
| 1 | 012345 | ENDOSCOPE | STOMACH | (REAL ENDOSCOPIC IMAGE) |
| 2 | 012345 | ENDOSCOPE | SMALL INTESTINE | (REAL ENDOSCOPIC IMAGE) |
| 3 | 012345 | ENDOSCOPE | LARGE INTESTINE | (VIRTUAL ENDOSCOPIC IMAGE) |
| 4 | 024680 | ENDOSCOPE | SMALL INTESTINE | (REAL ENDOSCOPIC IMAGE) |
| 5 | 024680 | ENDOSCOPE | SMALL INTESTINE | (REAL ENDOSCOPIC EXAMINATION REPORT) |
| 6 | 024680 | ENDOSCOPE | LARGE INTESTINE | (VIRTUAL ENDOSCOPIC IMAGE) |
| 7 | 024680 | ENDOSCOPE | LARGE INTESTINE | (IMAGE INTERPRETATION REPORT) |
| ... | ... | ... | ... | ... |

FIG.8

| CONDITION NO. | SYSTEM | DATABASE | DETAILED CONDITION |
|---|---|---|---|
| 1 | ENDOSCOPIC EXAMINATION SYSTEM | ENDOSCOPIC EXAMINATION DATABASE | ALL EXAMINATIONS |
| 2 | IMAGE DIAGNOSTIC SYSTEM | IMAGE DATABASE | VIRTUAL ENDOSCOPIC IMAGES |
| 3 | IMAGE DIAGNOSTIC SYSTEM | IMAGE INTERPRETATION REPORT DATABASE | THOSE RELATED TO VIRTUAL ENDOSCOPIC IMAGES IN IMAGE DATABASE |

FIG.10A

| START POINT REGION | END POINT REGION |
|---|---|
| MOUTH, NOSE | ESOPHAGUS, STOMACH, DUODENUM, SMALL INTESTINE, TRACHEA, TRACHEAL BRANCH |
| ANUS | LARGE INTESTINE, SMALL INTESTINE |

FIG.10B

| CHANGE PATTERN OF REGIONS ON TRAJECTORY |
|---|
| MOUTH/NOSE → ESOPHAGUS |
| MOUTH/NOSE → ESOPHAGUS → STOMACH |
| MOUTH/NOSE → ESOPHAGUS → STOMACH → DUODENUM |
| MOUTH/NOSE → ESOPHAGUS → STOMACH → DUODENUM → SMALL INTESTINE |
| MOUTH/NOSE → TRACHEA |
| MOUTH/NOSE → TRACHEA → TRACHEAL BRANCH |
| ANUS → RECTUM → LARGE INTESTINE |
| ANUS → RECTUM → LARGE INTESTINE → SMALL INTESTINE |

FIG.10C

| TRAJECTORY SHAPE MODEL | END POINT REGION |
|---|---|
| MODEL 01 (ORAL/NASAL ENDOSCOPE) | ESOPHAGUS |
| MODEL 01 (ORAL/NASAL ENDOSCOPE) | STOMACH |
| MODEL 01 (ORAL/NASAL ENDOSCOPE) | DUODENUM |
| MODEL 01 (ORAL/NASAL ENDOSCOPE) | SMALL INTESTINE |
| MODEL 01 (ORAL/NASAL ENDOSCOPE) | TRACHEA |
| MODEL 01 (ORAL/NASAL ENDOSCOPE) | TRACHEAL BRANCH |
| MODEL 02 (TRANSANAL ENDOSCOPE) | LARGE INTESTINE |
| MODEL 02 (TRANSANAL ENDOSCOPE) | SMALL INTESTINE |

FIG.10D

| CHANGE PATTERN OF REGIONS ON TRAJECTORY | MEDICAL INFORMATION OBTAINING CONDITION (GESTURE REGION) |
|---|---|
| MOUTH/ NOSE(COORDINATE VALUE RANGE)<br>→ ESOPHAGUS(COORDINATE VALUE RANGE) | ESOPHAGUS |
| MOUTH/NOSE(COORDINATE VALUE RANGE)<br>→ ESOPHAGUS(COORDINATE VALUE RANGE)<br>→ STOMACH (COORDINATE VALUE RANGE) | STOMACH |
| MOUTH/NOSE(COORDINATE VALUE RANGE)<br>→ ESOPHAGUS(COORDINATE VALUE RANGE)<br>→ STOMACH (COORDINATE VALUE RANGE)<br>→ DUODENUM (COORDINATE VALUE RANGE) | DUODENUM |
| MOUTH/NOSE(COORDINATE VALUE RANGE)<br>→ ESOPHAGUS(COORDINATE VALUE RANGE)<br>→ STOMACH (COORDINATE VALUE RANGE)<br>→ DUODENUM (COORDINATE VALUE RANGE)<br>→ SMALL INTESTINE (COORDINATE VALUE RANGE) | SMALL INTESTINE |
| MOUTH/NOSE(COORDINATE VALUE RANGE)<br>→ TRACHEA (COORDINATE VALUE RANGE) | TRACHEA |
| MOUTH/NOSE(COORDINATE VALUE RANGE)<br>→ TRACHEA (COORDINATE VALUE RANGE)<br>→ TRACHEAL BRANCH(COORDINATE VALUE RANGE) | TRACHEAL BRANCH |
| ANUS(COORDINATE VALUE RANGE)<br>→ RECTUM (COORDINATE VALUE RANGE)<br>→ LARGE INTESTINE (COORDINATE VALUE RANGE) | LARGE INTESTINE |
| ANUS(COORDINATE VALUE RANGE)<br>→ RECTUM (COORDINATE VALUE RANGE)<br>→ LARGE INTESTINE (COORDINATE VALUE RANGE)<br>→ SMALL INTESTINE (COORDINATE VALUE RANGE) | SMALL INTESTINE |

FIG.10E

| TRAJECTORY SHAPE/POSITION MODEL | MEDICAL INFORMATION OBTAINING CONDITION (GESTURE REGION) |
|---|---|
| MODEL 11 (UPPER GASTROINTESTINAL ENDOSCOPE/ESOPHAGUS) | ESOPHAGUS |
| MODEL 12 (UPPER GASTROINTESTINAL ENDOSCOPE/STOMACH) | STOMACH |
| MODEL 13 (UPPER GASTROINTESTINAL ENDOSCOPE/DUODENUM) | DUODENUM |
| MODEL 14 (ORAL/NASAL SMALL INTESTINE ENDOSCOPE) | SMALL INTESTINE |
| MODEL 15 (BRONCHOSCOPE/TRACHEA) | TRACHEA |
| MODEL 16 (BRONCHOSCOPE/TRACHEAL BRANCH) | TRACHEAL BRANCH |
| MODEL 17 (LARGE INTESTINE ENDOSCOPE) | LARGE INTESTINE |
| MODEL 18 (TRANSANAL SMALL INTESTINE ENDOSCOPE) | SMALL INTESTINE |

FIG.10F

| START POINT REGION | TRAJECTORY POSITION/SHAPE MODEL | MEDICAL INFORMATION OBTAINING CONDITION (GESTURE REGION) |
|---|---|---|
| MOUTH/NOSE | MODEL 11 (UPPER GASTROINTESTINAL ENDOSCOPE/ESOPHAGUS) | ESOPHAGUS |
| MOUTH/NOSE | MODEL 12 (UPPER GASTROINTESTINAL ENDOSCOPE/STOMACH) | STOMACH |
| MOUTH/NOSE | MODEL 13 (UPPER GASTROINTESTINAL ENDOSCOPE/DUODENUM) | DUODENUM |
| MOUTH/NOSE | MODEL 14 (ORAL/NASAL SMALL INTESTINE ENDOSCOPE) | SMALL INTESTINE |
| MOUTH/NOSE | MODEL 15 (BRONCHOSCOPE/TRACHEA) | TRACHEA |
| MOUTH/NOSE | MODEL 16 (BRONCHOSCOPE/TRACHEAL BRANCH) | TRACHEAL BRANCH |
| ANUS | MODEL 17 (LARGE INTESTINE ENDOSCOPE) | LARGE INTESTINE |
| ANUS | MODEL 18 (TRANSANAL SMALL INTESTINE ENDOSCOPE) | SMALL INTESTINE |

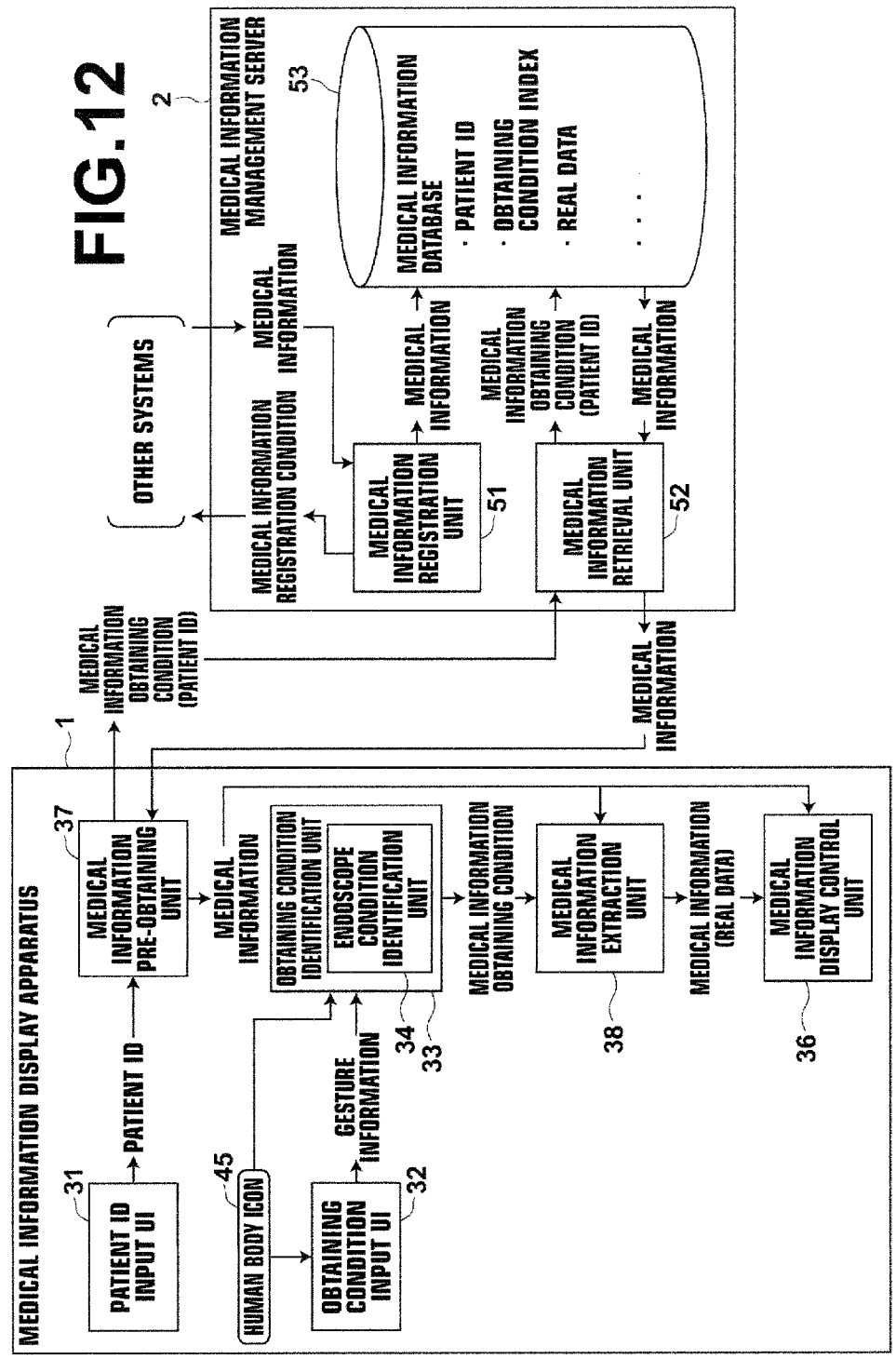

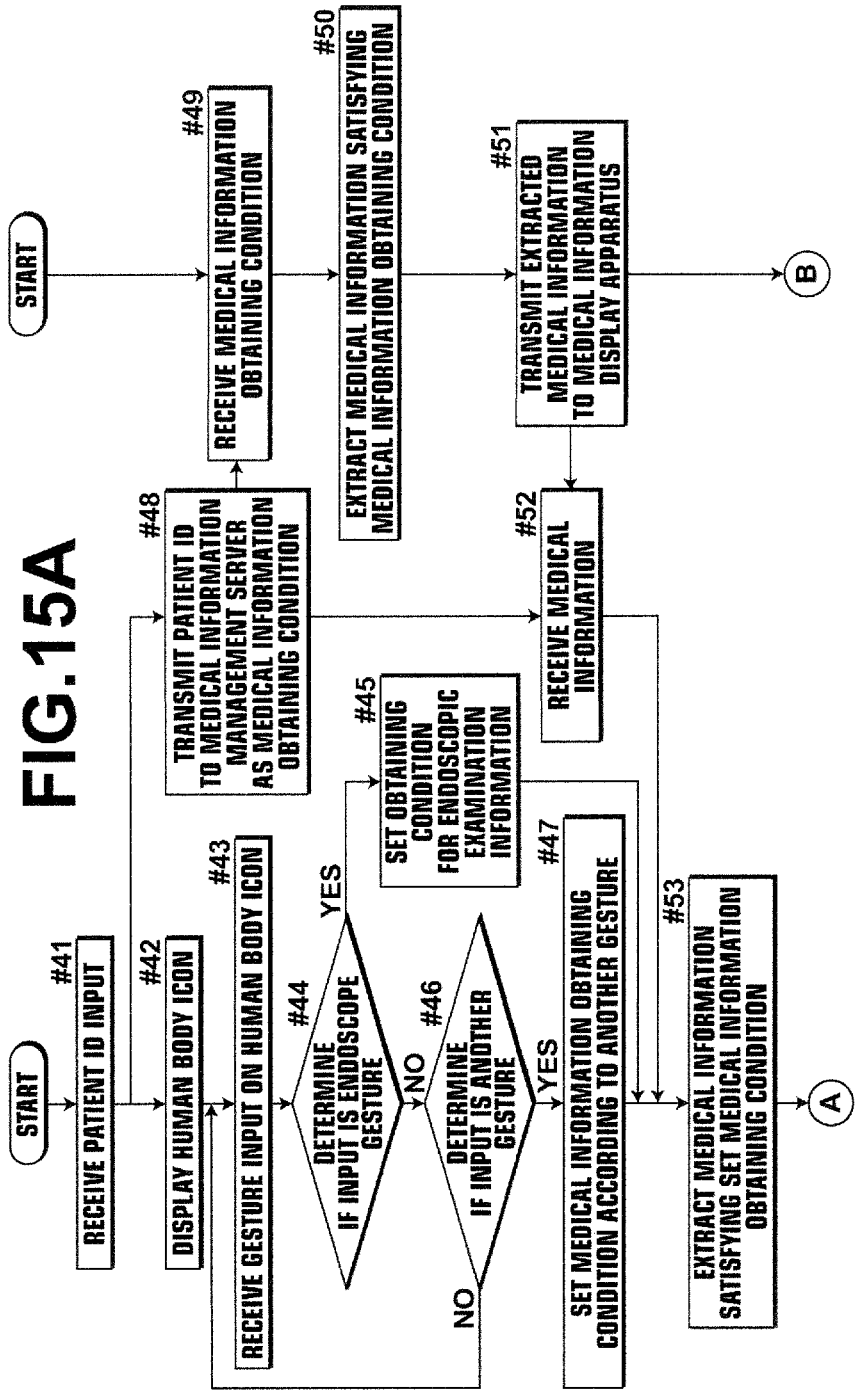

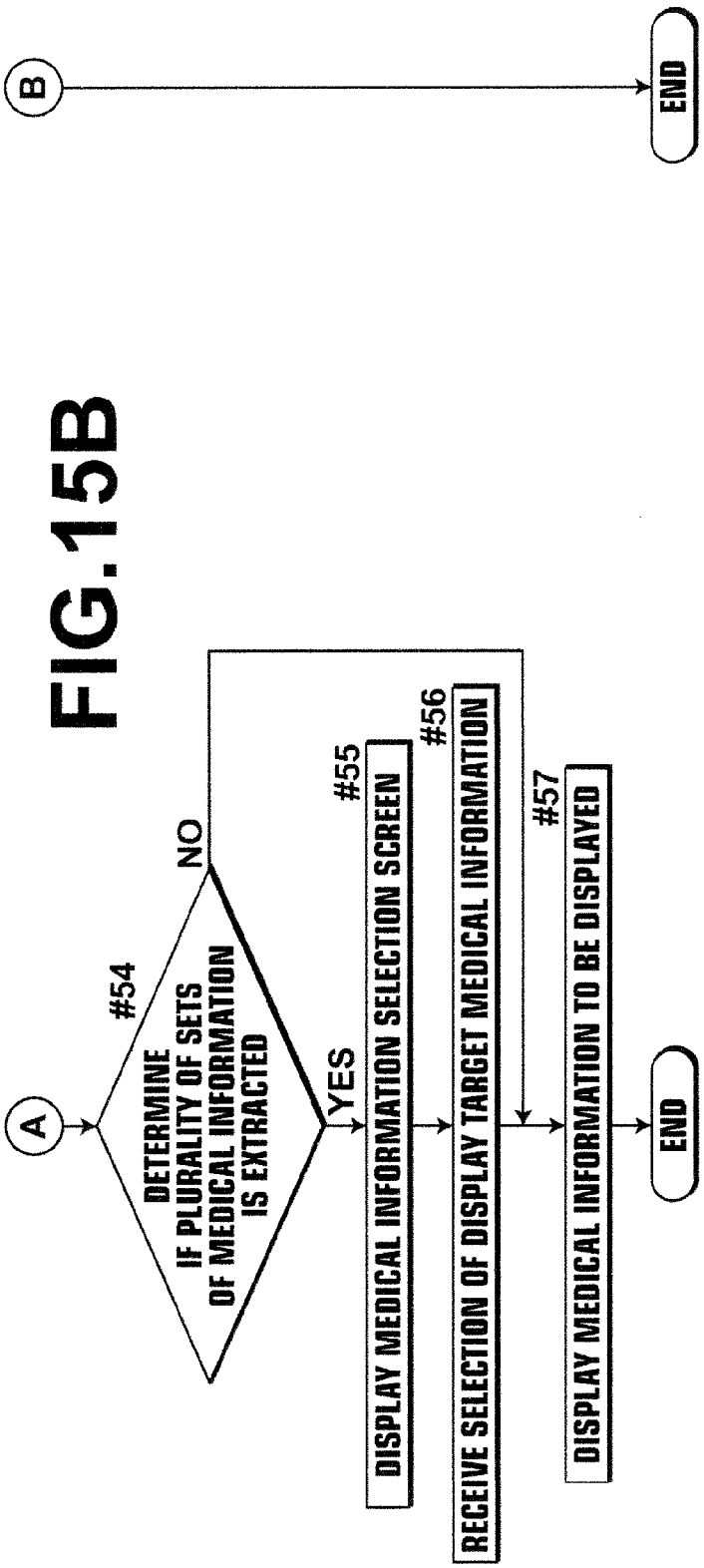

| INFORMATION NO. | PATIENT ID | INDEX INFORMATION | | SELECTION LIST INFORMATION | | | REAL DATA |
|---|---|---|---|---|---|---|---|
| | | GESTURE TYPE | GESTURE REGION | EXAMINATION DATE AND TIME | EXAMINATION TYPE | INFORMATION TYPE | |
| 11 | 001098 | ENDOSCOPE | LARGE INTESTINE | 10:19, AUGUST 2, 2009 | VIRTUAL ENDOSCOPIC EXAMINATION | IMAGE | (VIRTUAL ENDOSCOPIC IMAGE) |
| 12 | 001098 | ENDOSCOPE | LARGE INTESTINE | 10:19, AUGUST 2, 2009 | VIRTUAL ENDOSCOPIC EXAMINATION | REPORT | (IMAGE INTERPRETATION REPORT) |
| 13 | 001098 | ENDOSCOPE | LARGE INTESTINE | 09:36, AUGUST 9, 2009 | REAL ENDOSCOPIC EXAMINATION | IMAGE | (REAL ENDOSCOPIC IMAGE) |
| 14 | 001098 | ENDOSCOPE | LARGE INTESTINE | 09:36, AUGUST 9, 2009 | REAL ENDOSCOPIC EXAMINATION | REPORT | (REAL ENDOSCOPIC EXAMINATION REPORT) |
| 15 | 001098 | ENDOSCOPE | LARGE INTESTINE | 17:20, JULY 30, 2010 | REAL ENDOSCOPIC EXAMINATION | IMAGE | (REAL ENDOSCOPIC IMAGE) |
| 16 | 001098 | ENDOSCOPE | SMALL INTESTINE | 11:45, AUGUST 2, 2009 | REAL ENDOSCOPIC EXAMINATION | IMAGE | (REAL ENDOSCOPIC IMAGE) |
| 17 | 012345 | ENDOSCOPE | STOMACH | 11:06, JUNE 9, 2010 | REAL ENDOSCOPIC EXAMINATION | IMAGE | (REAL ENDOSCOPIC IMAGE) |
| 18 | 012345 | ENDOSCOPE | SMALL INTESTINE | 11:18, JUNE 21, 2010 | REAL ENDOSCOPIC EXAMINATION | IMAGE | (REAL ENDOSCOPIC IMAGE) |
| 19 | 012345 | ENDOSCOPE | LARGE INTESTINE | 10:51, JULY 2, 2010 | VIRTUAL ENDOSCOPIC EXAMINATION | IMAGE | (VIRTUAL ENDOSCOPIC IMAGE) |
| ⋮ | ⋮ | ⋮ | ⋮ | ⋮ | ⋮ | ⋮ | ⋮ |

TOUCH MEDICAL INFORMATION YOU WANT TO DISPLAY

PATIENT ID: 001098  MEDICAL INFORMATION : ENDOSCOPE/LARGE INTESTINE
OBTAINING CONDITION

| No. | EXAMINATION DATE AND TIME | EXAMINATION TYPE | INFORMATION TYPE |
|---|---|---|---|
| 001 | 10:19, AUGUST 2, 2009 | VIRTUAL ENDOSCOPIC EXAMINATION | IMAGE |
| 002 | 10:19, AUGUST 2, 2009 | VIRTUAL ENDOSCOPIC EXAMINATION | REPORT |
| 003 | 09:36, AUGUST 9, 2009 | REAL ENDOSCOPIC EXAMINATION | IMAGE |
| 004 | 09:36, AUGUST 9, 2009 | REAL ENDOSCOPIC EXAMINATION | REPORT |
| 005 | 17:20, JULY 30, 2010 | REAL ENDOSCOPIC EXAMINATION | IMAGE |

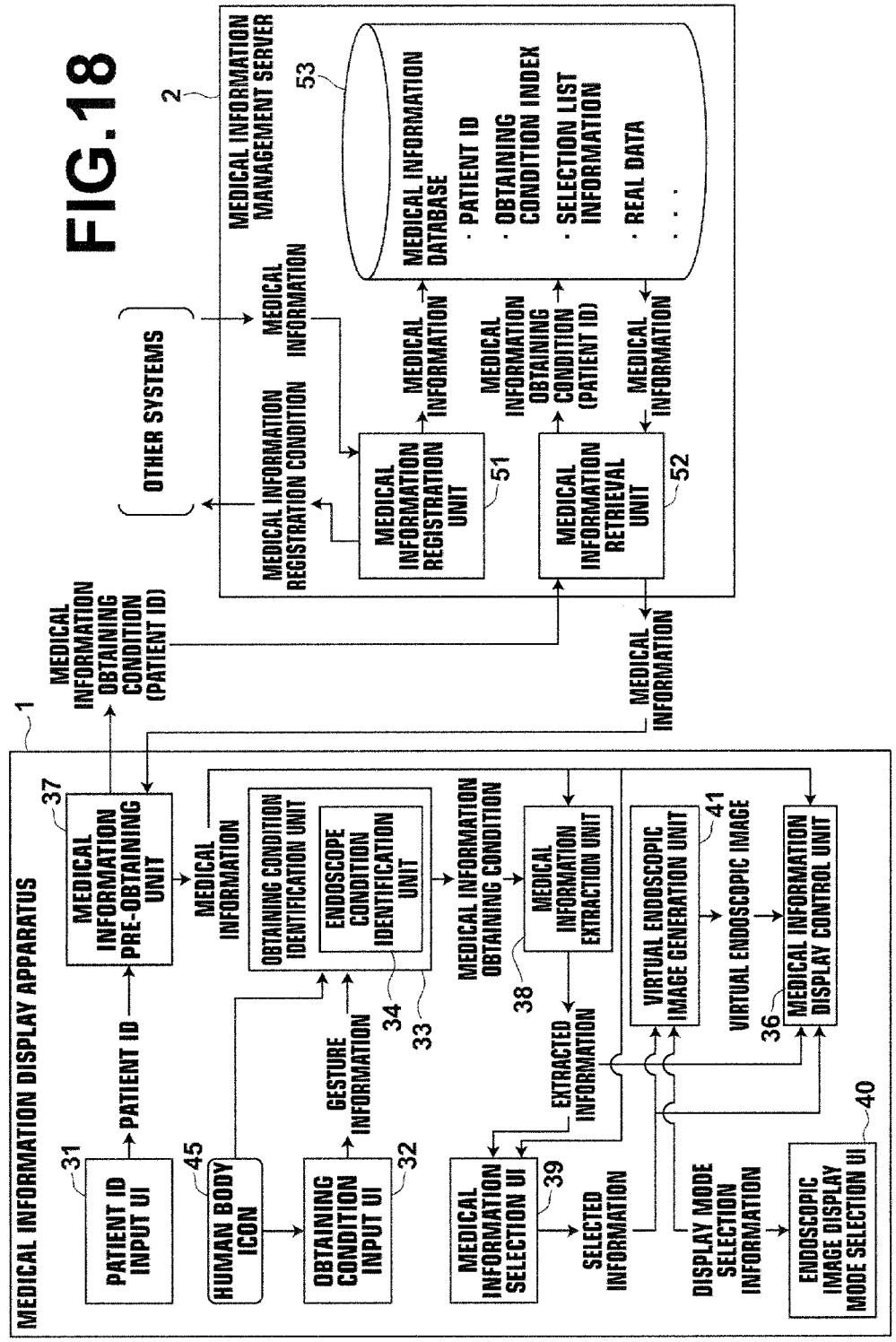

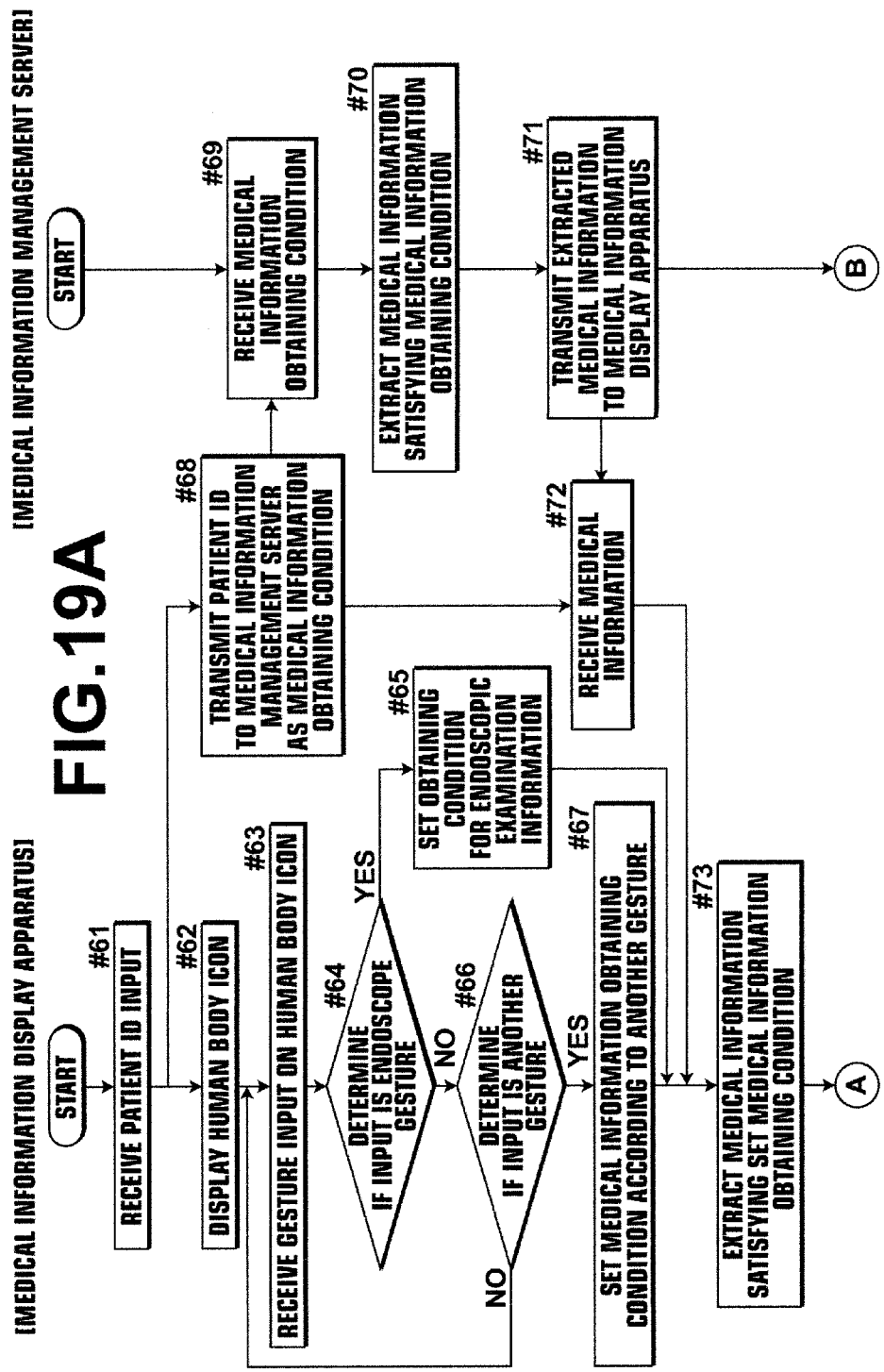

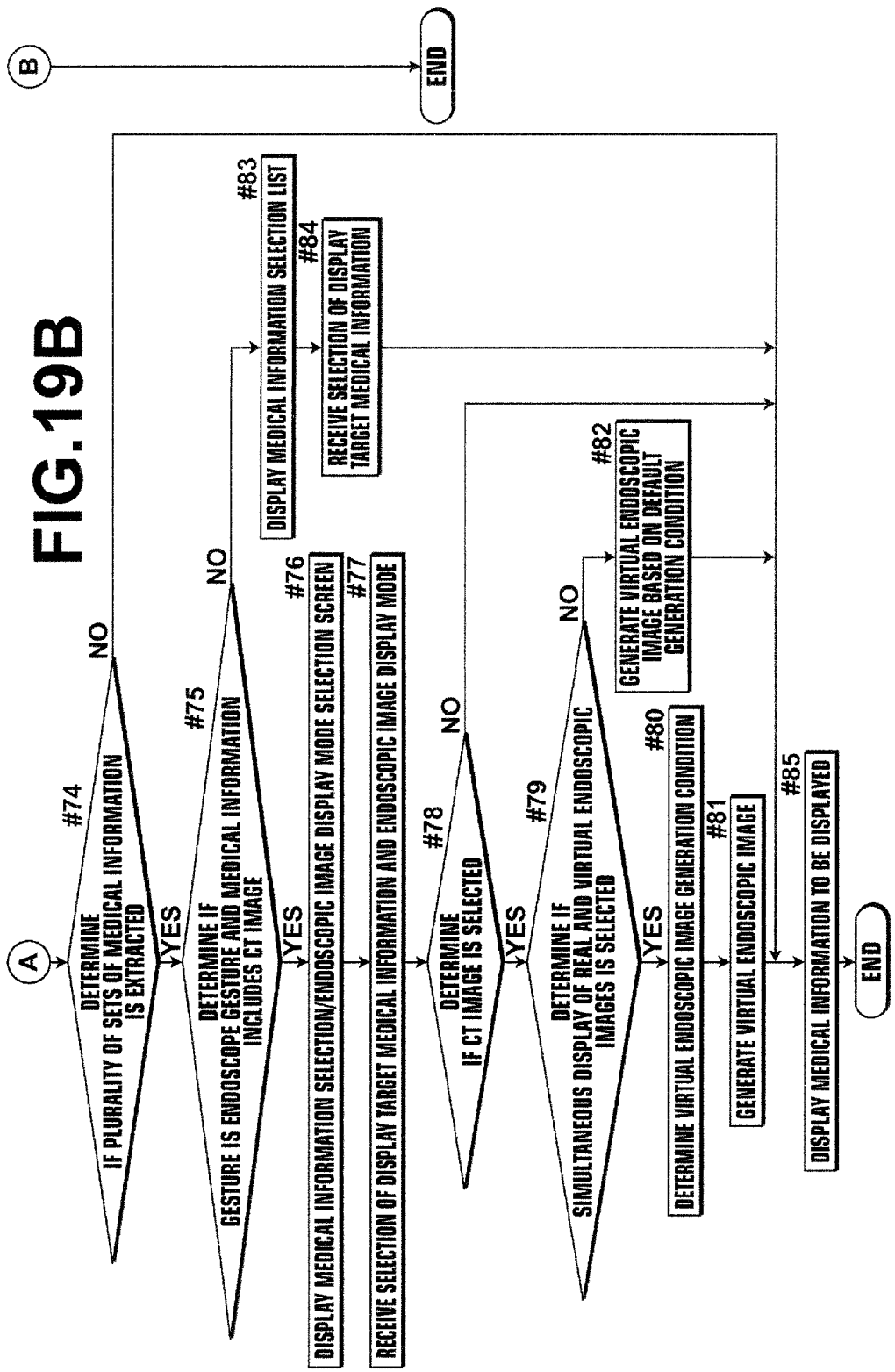

FIG.20

| INFORMATION NO. | PATIENT ID | INDEX INFORMATION | | SELECTION LIST INFORMATION | | | REAL DATA |
|---|---|---|---|---|---|---|---|
| | | GESTURE TYPE | GESTURE REGION | EXAMINATION DATE AND TIME | MODALITY TYPE | INFORMATION TYPE | |
| 11 | 001098 | ENDOSCOPE | LARGE INTESTINE | 10:19, AUGUST 2, 2009 | CT | IMAGE | (CT IMAGE) |
| 12 | 001098 | ENDOSCOPE | LARGE INTESTINE | 10:19, AUGUST 2, 2009 | CT | REPORT | (IMAGE INTERPRETATION REPORT) |
| 13 | 001098 | ENDOSCOPE | LARGE INTESTINE | 09:36, AUGUST 9, 2009 | REAL ENDOSCOPE | IMAGE | (REAL ENDOSCOPIC IMAGE) |
| 14 | 001098 | ENDOSCOPE | LARGE INTESTINE | 09:36, AUGUST 9, 2009 | REAL ENDOSCOPE | REPORT | (REAL ENDOSCOPIC EXAMINATION REPORT) |
| 15 | 001098 | ENDOSCOPE | LARGE INTESTINE | 17:20, JULY 30, 2010 | REAL ENDOSCOPE | IMAGE | (REAL ENDOSCOPIC IMAGE) |
| 16 | 012345 | ENDOSCOPE | STOMACH | 11:06, JUNE 9, 2010 | REAL ENDOSCOPE | IMAGE | (REAL ENDOSCOPIC IMAGE) |
| 17 | 012345 | ENDOSCOPE | SMALL INTESTINE | 11:18, JUNE 21, 2010 | REAL ENDOSCOPE | IMAGE | (REAL ENDOSCOPIC IMAGE) |
| 18 | 012345 | ENDOSCOPE | LARGE INTESTINE | 10:51, JULY 2, 2010 | CT | IMAGE | (CT IMAGE) |
| ⋮ | ⋮ | ⋮ | ⋮ | ⋮ | ⋮ | ⋮ | ⋮ |

FIG.21

TOUCH MEDICAL INFORMATION YOU WANT TO DISPLAY

PATIENT ID: 001098    MEDICAL INFORMATION : ENDOSCOPE/LARGE INTESTINE
OBTAINING CONDITION

| No. | EXAMINATION DATE AND TIME | MODALITY | INFORMATION TYPE |
|-----|---------------------------|----------|------------------|
| 001 | 10:19, AUGUST 2, 2009 | CT | IMAGE |
| 002 | 10:19, AUGUST 2, 2009 | CT | REPORT |
| 003 | 09:36, AUGUST 9, 2009 | REAL ENDOSCOPE | IMAGE |
| 004 | 09:36, AUGUST 9, 2009 | REAL ENDOSCOPE | REPORT |
| 005 | 17:20, JULY 30, 2010 | REAL ENDOSCOPE | IMAGE |

☑ SIMULTANEOUS DISPLAY OF REAL AND VIRTUAL ENDOSCOPIC IMAGES

MEDICAL INFORMATION DISPLAY APPARATUS, METHOD, AND PROGRAM

TECHNICAL FIELD

The present invention relates to a technology that allows a user to display desired medical information using an intuitive user interface, such as a touch panel.

BACKGROUND ART

In medical sites, a wide variety of medical information is generated, including waveform information, such as electrocardiograms, electroencephalograms, and the like, numerical information, such as blood pressures, body temperatures, and the like, and textual information, such as various examination reports, medical records, and the like, as well as image information obtained by various modalities, such as CT, MRI, US, PET, and the like.

For example, in the case of endoscopic examination, various types of endoscopes according to regions of a subject are available, such as bronchoscope, gastrointestinal endoscope, thoracoscope, arthroscope, and the like, whereby various endoscopic images are obtained, and endoscopic examination reports which include findings of the obtained endoscopic images and the like are generated. Further, if pixel values are projected by a central projection method with three-dimensional volume data obtained by CT or the like as input, a virtual endoscopic image representing inside of a subject observed by a virtual endoscope may be obtained. The generated endoscopic image is used for image diagnosis and image interpretation report is generated.

Some medical institutions have established a system for managing such medical information. For example, such medical information is stored in a database as electronic data, then medical information desired by a user is selected in response to a request from a client terminal, and the selected information is displayed on a display device connected to the client terminal.

In order to improve the operability of selection and display of such medical information, various user interfaces are proposed. For example, such a user interface is known as described, for example, in Japanese Unexamined Patent Publication No. 2005-080969 in which, when selecting a given region of a patient, the user is allowed to select a broad region from a GUI using a human body icon displayed on a display device to display detailed region information on the display device and to select a desired detailed region from the displayed detailed region information.

Further, another user interface is known as described, for example, in Japanese Unexamined Patent Publication No. 2009-119000 in which the user is allowed to draw a reference line in an axial cross-sectional image by a touch operation using an input device having a touch screen display connected to and used with a medical image processing workstation and, when drawn, a coronal cross-sectional image with the reference line as the cutting plane is generated and displayed.

DISCLOSURE OF THE INVENTION

The user interface described in Japanese Unexamined Patent Publication No. 2005-080969, however, allows intuitive selection of only a broad region and it is not always the case that the range of required medical information is intuitively narrowed down appropriately and rapidly only by such selection of a broad region in view of the fact that a wide variety of medical information is generated in medical sites as described above. The user interface described in Japanese Unexamined Patent Publication No. 2009-119000 is an interface intended to switch an already selected image to another and not for appropriately narrowing down the range of required medical information.

The present invention has been developed in view of the circumstances described above, and it is an object of the present invention to provide a medical information display apparatus, system, and method that allows a user to obtain medical information with respect to real and/or virtual endoscopic examinations by more intuitive and easier operation. It is a further object of the present invention to provide a medical information display control program.

A medical information display apparatus of the present invention is an apparatus, including:

a display means for displaying given information;

a gesture input means for detecting a gesture operation performed on a display surface of the display means and outputting gesture information representing a content of the detected gesture operation;

a first display control means for displaying a subject appearance image representing an appearance of a subject at a predetermined display position of the display means;

an obtaining condition identification means for identifying a medical information obtaining condition for obtaining medical information with respect to the subject based on gesture information outputted according to a gesture operation detected by the gesture input means while the subject appearance image is displayed and display position information of the subject appearance image;

a medical information obtaining means for selectively obtaining medical information satisfying the identified medical information obtaining condition from a medical information storage means storing a plurality of sets of medical information; and a second display control means for displaying the obtained medical information on the display means, wherein the obtaining condition identification means includes an endoscope condition identification means for identifying a medical information obtaining condition for obtaining medical information with respect to an actual and/or a virtual endoscopic examination of the subject when the display position information of the subject appearance image and gesture trajectory information included in the gesture information outputted according to the gesture operation while the subject appearance image is displayed and representing a trajectory of the gesture operation satisfy an endoscope gesture condition representing an insertion operation of an endoscope in the subject represented by the subject appearance image.

A medical information display system of the present invention is a system in which a medical information supply apparatus for selectively supplying medical information of a subject based on a given medical information obtaining condition and a medical information display apparatus of the present invention are communicatively linked via a network. Here, the medical information supply apparatus may be an apparatus that includes: a medical information storage means storing a plurality of sets of medical information in a data structure that allows selection of medical information based on a given medical information obtaining condition; an obtaining condition receiving means for receiving a medical information obtaining condition from the medical information display apparatus; a medical information retrieval means for obtaining medical information satisfying the received medical information obtaining condition from the medical information storage means; and a medical information transmission means for transmitting the obtained medical information to the medical information display apparatus that has transmitted the medical information obtaining condition.

A medical information display method of the present invention is a method, including:

a step of displaying a subject appearance image representing an appearance of a subject on a display means;

a step of receiving input of a gesture performed on a display surface of the display means while the subject appearance image is displayed and outputting gesture position information representing a position of the inputted gesture on the display surface;

a step of identifying a medical information obtaining condition for obtaining medical information of the subject based on the outputted gesture position information and a position of the subject appearance image on the display surface;

a step of selectively obtaining medical information satisfying the identified medical information obtaining condition from a medical information storage means storing a plurality of sets of medical information; and a step of displaying the obtained medical information, wherein the step of identifying medical information obtaining condition includes a step of recognizing an endoscope gesture representing an insertion path of an endoscope in the subject represented by the subject appearance image and, if the endoscope gesture is recognized, identifying a medical information obtaining condition for obtaining medical information of an actual and/or a virtual endoscopic examination of the subject.

A medical information display control program of the present invention is a program for causing a computer to perform:

a step of displaying a subject appearance image representing an appearance of a subject on a display means;

a step of receiving input of a gesture performed on a display surface of the display means while the subject appearance image is displayed and outputting gesture position information representing a position of the inputted gesture on the display surface;

a step of identifying a medical information obtaining condition for obtaining medical information of the subject based on the outputted gesture position information and a position of the subject appearance image on the display surface;

a step of selectively obtaining medical information satisfying the identified medical information obtaining condition from a medical information storage means storing a plurality of sets of medical information; and a step of displaying the obtained medical information, wherein, in the step of identifying medical information obtaining condition, the program causes the computer to perform a step of recognizing an endoscope gesture representing an insertion path of an endoscope in the subject represented by the subject appearance image and, if the endoscope gesture is recognized, identifying a medical information obtaining condition for obtaining medical information of an actual and/ or a virtual endoscopic examination of the subject.

Here, as for a specific example of the subject appearance image, an image schematically representing the subject may be cited. The subject appearance image may be an image in which region identification information for identifying a region of the subject is related to position information of each position of the image.

A determination as to whether or not the endoscope gesture condition is satisfied and/or identification of the medical information obtaining condition with respect to the endoscopic examination may be made based on at least one of a position close to a start point of trajectory of the gesture operation on the subject represented by the subject appearance image, a position of an end point of the gesture on the subject represented by the subject appearance image, trajectory passing positions which are positions of a plurality of points of the gesture on the subject represented by the subject appearance image, and a shape of the gesture.

If a real endoscopic image formed through imaging with an actual endoscope and a virtual endoscopic image reconstructed from a three-dimensional medical image of the subject and representing a body cavity of the subject viewed from a given position within the body cavity are obtained as medical information satisfying the medical information obtaining condition for obtaining medical information with respect to the endoscopic examination, the real endoscopic image and virtual endoscopic image may be displayed simultaneously. Further, an arrangement may be adopted in which selection as to whether or not to perform simultaneous display of the real endoscopic image and virtual endoscopic image is received in advance.

An arrangement may be adopted in which, if a medical image representing the subject is obtained from the medical information storage means, predetermined image processing is performed on the obtained medical image as required, and, if a three-dimensional medical image representing the subject is obtained as medical information satisfying the medical information obtaining condition for obtaining medical information with respect to the virtual endoscopic examination, a virtual endoscopic image viewed from a given position within a body cavity of the subject and representing the body cavity is generated based on the three-dimensional medical image and the generated virtual endoscopic image is displayed.

An arrangement may be adopted in which, if a plurality of sets of medical information satisfying the medical information obtaining condition is obtained, the plurality of sets of medical information is list displayed on the display means and selection of display target medical information is received. Here, the plurality of sets of medical information may be those representing examinations performed at different times or different regions of the subject. Further, when performing the list display, the plurality of sets of medical information may be displayed in the form of thumbnails or icons.

According to the present invention, the following are performed: receiving, while the subject appearance image is displayed on the display means, input of a gesture performed on the display surface, recognizing an endoscope gesture representing an insertion path of an endoscope in the subject represented by the subject appearance image based on position information of the gesture and a position of the subject appearance image on the display surface, identifying, if the endoscope gesture is recognized, a medical information obtaining condition for obtaining medical information of an actual and/or a virtual endoscopic examination of the subject, selectively obtaining medical information satisfying the identified medical information obtaining condition from the medical information storage means storing a plurality of sets of medical information, and displaying the obtained medical information. Thus, a user is allowed to obtain medical information with respect to an endoscopic examination through a more intuitive and easier operation.

BRIEF DESCRIPTION OF DRAWINGS

FIG. 7 illustrates, by way of example, a data structure of a medical information database and an example of registered data in the first embodiment and a second embodiment of the present invention.

FIG. 8 illustrates a table that summaries registration conditions of endoscope related information registered in the medical information database.

FIG. 10A is a table representing a first example of reference data used for determining an endoscope gesture.

FIG. 10B is a table representing a second example of reference data used for determining an endoscope gesture.

FIG. 10C is a table representing a third example of reference data used for determining an endoscope gesture.

FIG. 10D is a table representing a fourth example of reference data used for determining an endoscope gesture.

FIG. 10E is a table representing a fifth example of reference data used for determining an endoscope gesture.

FIG. 10F is a table representing a sixth example of reference data used for determining an endoscope gesture.

FIG. 12 is a block diagram of the medical information display apparatus and medical information management server, schematically illustrating the functions implemented therein in the second embodiment.

FIG. 15A is a flowchart illustrating a processing flow for displaying medical information performed in the medical information integration system in the third embodiment of the present invention (first half).

FIG. 15B is a flowchart illustrating a processing flow for displaying medical information performed in the medical information integration system in the third embodiment of the present invention (second half).

FIG. 16 illustrates, by way of example, a data structure of the medical information database and an example of registered data in the third embodiment of the present invention.

FIG. 17A illustrates, by way of example, a medical information selection screen.

FIG. 18 is a block diagram of the medical information display apparatus and medical information management server, schematically illustrating the functions implemented therein in a fourth embodiment of the present invention.

FIG. 19A is a flowchart illustrating a processing flow for displaying medical information performed in the medical information integration system in the fourth embodiment of the present invention (first half).

FIG. 19B is a flowchart illustrating a processing flow for displaying medical information performed in the medical information integration system in the fourth embodiment of the present invention (second half).

FIG. 20 illustrates, by way of example, a data structure of the medical information database and an example of registered data in the fourth embodiment of the present invention.

FIG. 21 illustrates, by way of example, a medical information selection/endoscopic image display mode selection screen.

BEST MODE FOR CARRYING OUT THE INVENTION

Figure 1:
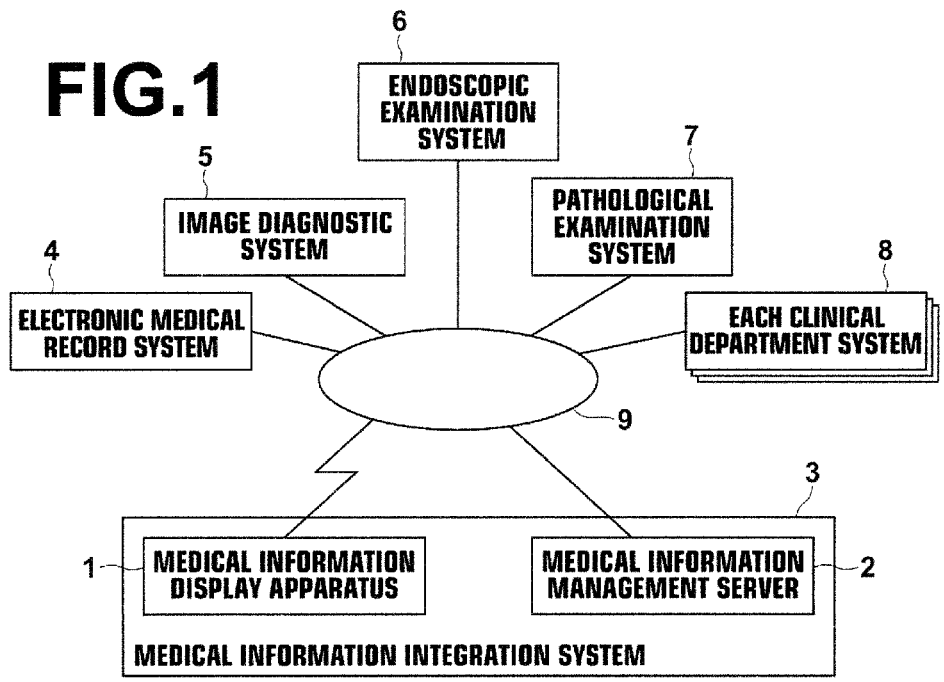
FIG. 1 illustrates a configuration of a medical information integration system, which includes a medical information display apparatus according to an embodiment of the present invention, and peripheral systems.

FIG. 1 illustrates a configuration of a medical information integration system 3, which includes a medical information display apparatus 1 according to an embodiment of the present invention, and peripheral systems. As illustrated in the drawing, the medical information integration system 3 is communicatively linked to an electronic medical record system 4, an image diagnostic system 5, an endoscopic examination system 6, a pathological examination system 7, and each clinical department system 8 via a network 9. The medical information integration system 3 includes the medical information display apparatus 1 according to an embodiment of the present invention and a medical information management server 2.

In the present embodiment, medical information generated in the electronic medical record system 4, the image diagnostic system 5, the endoscopic examination system 6, the pathological examination system 7, and the each clinical department system 8 is integrally collected and managed by the medical information management server 2. The medical information display apparatus 1 makes a request for desired medical information to the medical information management server 2 and displays medical information satisfying the request supplied from the medical information management server 2.

Figure 2:
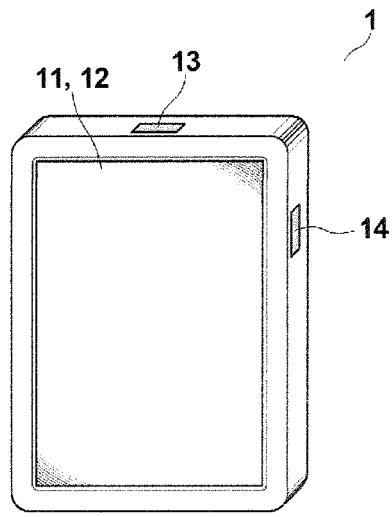
FIG. 2 schematically illustrates an external view of the medical information display apparatus according to an embodiment of the present invention.
Figure 3:
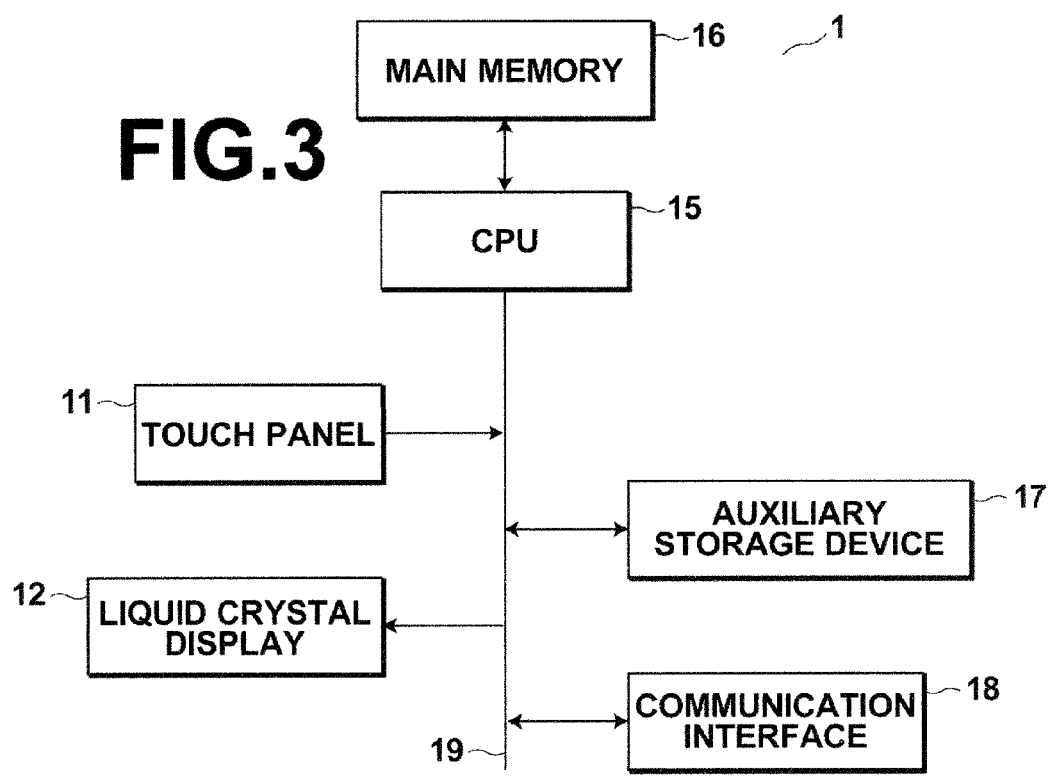
FIG. 3 is a block diagram of the medical information display apparatus according to an embodiment of the present invention, illustrating major components thereof.

FIG. 2 schematically illustrates an appearance of the medical information display apparatus 1 according to an embodiment of the present invention, and FIG. 3 is a block diagram of the medical information display apparatus 1, illustrating major components thereof.

As illustrated in FIG. 2, the medical information display apparatus 1 includes a liquid crystal display 12 integrally formed with a touch panel 11 on the front side with an antenna unit 13 for wireless communication and a power switch 14 on side surfaces.

As illustrated in FIG. 3, the medical information display apparatus 1 is of a configuration in which a CPU 15, a main memory 16, an auxiliary storage device 17, the touch panel 11, the liquid crystal display 12, a communication interface 18, and the like are linked via a data bus.

The CPU 15 performs each processing by loading middleware, such as an operating system and the like, and each program, such as application software for obtaining and displaying medical information of the present invention, stored in the auxiliary storage device 17 to the main memory 16. This allows receiving of user input via the touch panel 11, input/output control, such as display control of various types of information, including medical information, on the liquid crystal display 12, communication via the communication interface 18, and the like.

As for the auxiliary storage device 17, a well-known flash memory drive (SSD: Solid State Drive) or a hard disk drive (HDD) is used. The auxiliary storage device 17 includes each program described above installed therein. The application software for displaying medical information of the present invention may be installed from a recording medium, such as CD-ROM or the like, using a disk drive connected to the medical information display apparatus 1 or installed after downloaded from a storage device of a server linked to the apparatus 1 via a network, such as the Internet or the like. Further, the auxiliary storage device 17 is used for temporarily storing medical information obtained from the medical information management server 2.

As for the touch panel 11, any known type may be used, including resistive type, capacitive type, electromagnetic type, surface elastic (ultrasonic) wave type, infrared type, and the like. Further, a touch panel capable of detecting a multi-touch, i.e., touches at a plurality of positions, such as a projected capacitive touch panel, may be used. Touch operations are performed with a finger of the user or with a predetermined pen or the like. The touch panel 11 detects the start of touching thereon, movement of the touched position, and end of the touching at a time interval defined by the control program, and outputs information of detected touch type and touched position at the time in a coordinate system of the touch panel 11. The term "start of touching" as used herein refers to a touching operation to a new position on the touch panel 11, the term "movement of touched position" refers to a moving operation of the touched position with the touch panel 11 being kept touched, and the term "end of touching" refers to a removing operation from the touch panel. This allows a gesture operation depicting a trajectory on the touch panel 11 to be detected as a sequence of points. That is, a series of operations for depicting a trajectory from the start of touching, movement of the touched position, and end of the touching is detected as one gesture operation and information of a plurality of positions detected at each time point of the series of operations is obtained as gesture information. The correspondence relationship between the coordinate system of the touch panel 11 and the coordinate system of the liquid crystal display 12 is identified through calibration at the time when the medical information display apparatus 1 is manufactured, so that a mutual coordinate conversion is possible. Hereinafter, the coordinate system of the liquid crystal display 12 and the coordinate system of the touch panel 11 are assumed to be the same coordinate system and referred to as the coordinate system of the display apparatus in order to simplify the description.

The communication interface 18 controls communication through a well-known mobile communication network, wireless LAN, and the like. In the present embodiment, communication with the medical information management server 2 is performed via the communication interface 18.

In the mean time, the information management server 2 is a computer having a medical information database. As for the hardware configuration, it includes an external storage device in addition to well-known hardware devices, including CPU, main memory, auxiliary storage device, I/O interface, communication interface, data bus, and the like. The medical information management server 2 is provided with application software for medical information registration in and extraction from the database, as well as a well-known operating system and database management software. Such software is installed from a recording medium, such as CD-ROM or the like, or after downloaded from a storage device of a server linked thereto via a network, such as the Internet or the like.

The electronic medical record system 4 employs a known computer system and is of a configuration in which, for example, a terminal of the each clinical department and the like, and an electronic medical record management server having an electronic medical record database in which electronic medical record information is stored are communicatively linked via a network. Electronic medical record information inputted from a terminal of each clinical department and the like is managed using the electronic medical record database. For example, the electronic medical record includes: patient information, such as name, date of birth, gender, and the like of a patient; examination history information, such as date of each examination received, contents, results, and the like; diagnostic history, such as date of diagnosis received, major complaint, determined disease name, and the like; and treatment history information, such as date of operation, procedure, or medication and the like. In the present embodiment, the electronic medical record database has a database structure in which a patient ID for identifying each patient is related to the aforementioned electronic medical record.

The image diagnostic system 5 also employs a known computer system and is of a configuration in which, for example, an image diagnostic medical workstation, an image management server having a database storing image data captured by modalities, such as CT, MRI, and the like, and an image interpretation report server having an image interpretation report database storing image interpretation reports of image interpretation results of the captured images are communicatively linked via a network. Here, the image diagnosis medical workstation is capable of performing known image processing such as MIP, MPR, CPR, volume rendering, or the like according to the purpose or target of the diagnosis in combination with a known image analysis, such as bone extraction/elimination, blood vessel extraction, organ extraction, detection of abnormal tissue pattern, or the like, and these processed/analyzed images are also stored in the image database. The image data may include both two-dimensional images (pixel data) and three-dimensional images (voxel data), and both still images and moving images. In addition to the patient ID, the image database includes other auxiliary information related to each image, such as an image ID for identifying each image, modality information by which the image is obtained, region information of a subject in the image, and the like. The modality information is provided by the modality at the time of image generation. The region information of a subject may be provided by the modality at the time of image generation based on the examination order or the like or, if the image is a tomographic image, such as a CT image or the like, the region information may be provided by the image diagnosis medical workstation for each slice using a well-known region recognition technique, such as that described in Japanese Unexamined Patent Publication No. 2008-259682. The image interpretation report database has a database structure in which each image interpretation report, patient ID, and image ID of an interpretation target image are related to each other. Each image data or image interpretation report may be indirectly related to the patient ID by way of examination ID for identifying each examination (imaging).

The endoscopic examination system 6 also employs a known computer system and includes an endoscopic examination management server with an endoscopic examination database having therein real endoscopic images obtained by various types of endoscopes, endoscopic examination reports which include summaries of endoscopic examination results, and the like related to the examination IDs and patient IDs, and access control to the endoscopic examination database is performed by the server.

The pathological examination system 7 also employs a known computer system and includes a pathological examination management server with a pathological examination database having therein microscope images obtained by pathological examinations, pathological examination reports which include summaries of pathological examination results, and the like related to examination IDs and patient IDs, and access control to the pathological examination database is performed by the server.

The each clinical department system 8 includes a management server of each clinical department with a database of each clinical department having therein examination data, examination reports, and the like unique to each clinical department related to the examination IDs and patient IDs, and access control to the database of each clinical department is performed by each server. The examination data unique to each clinical department may be, for example, electrocardiogram data and the like (waveforms, numerical values, or the like) if the clinical department is a cardiovascular department, auditory test data and the like (waveforms, numerical values, or the like) if the department is an otolaryngology department, or visual acuity test data, fundus examination data or the like (numerical values, or the like) if the department is an ophthalmology department.

In the present embodiment, the endoscopic examination system 6 and pathological examination system 7 are systems separate from the each clinical department system 8, but they may be integrated as a part of the each clinical department system 8. In this case, information of endoscopic examinations and pathological examinations is managed as examination data of each clinical department according to the content of each examination.

Figure 4:
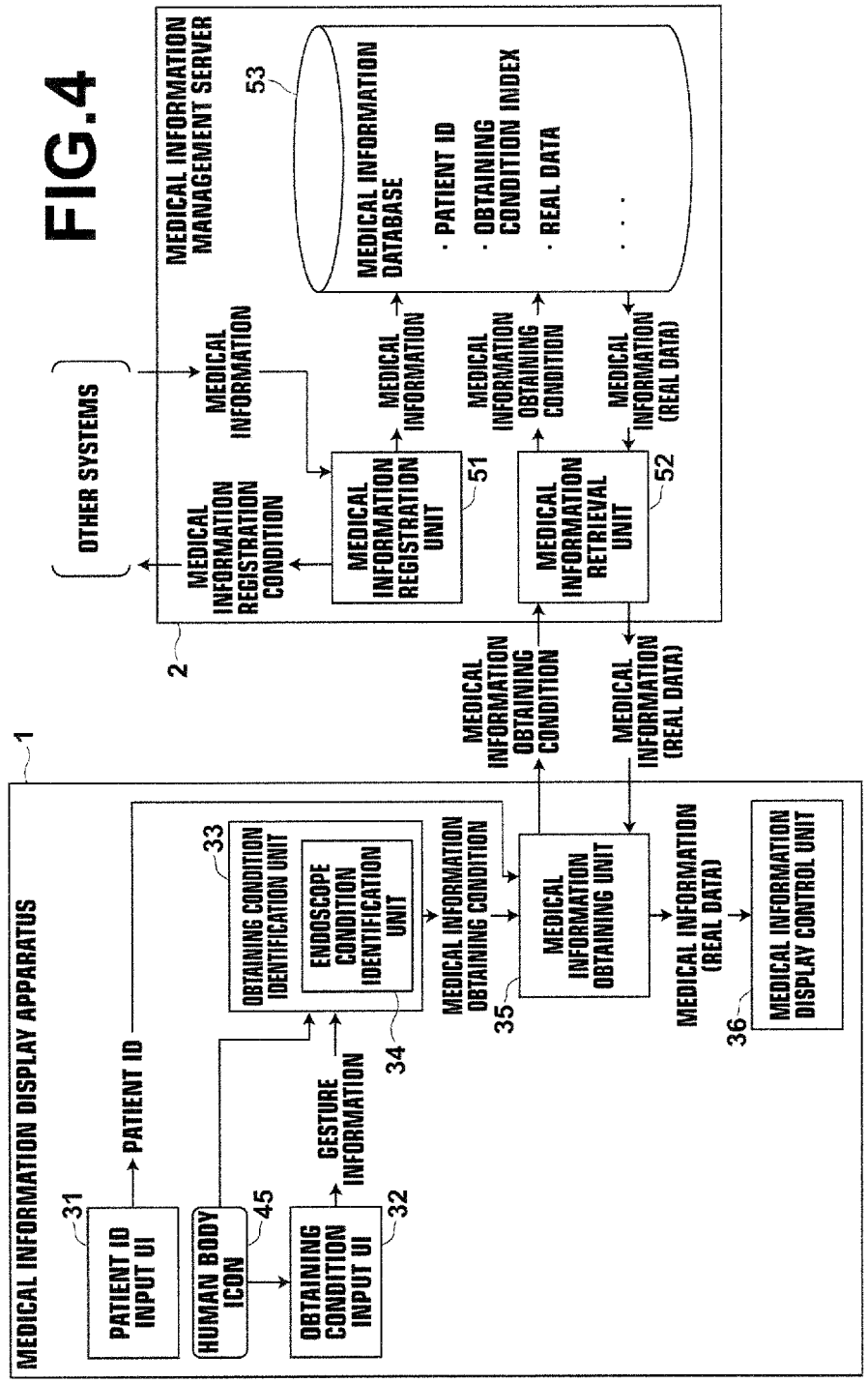
FIG. 4 is a block diagram of the medical information display apparatus and medical information management server, schematically illustrating the functions implemented therein in a first embodiment.

A first embodiment of the present invention is an embodiment in which medical information of endoscopic examination (endoscope related information) is obtained from the medical information management server 2 according to a touch panel operation representing an endoscope performed in the medical information display apparatus 1 and displayed on the liquid crystal display 12. FIG. 4 is a block diagram of the medical information display apparatus 1 and medical information management server 2, schematically illustrating the functions implemented therein in the first embodiment. As illustrated in the drawing, medical information display apparatus of the present invention includes a patient ID input user interface (UI) 31, an obtaining condition input UI 32, an obtaining condition identification unit 33, a medical information obtaining unit 35, a medical information display control unit 36, and a human body icon 45. The obtaining condition identification unit 33 includes an endoscope condition identification unit 34. The patient ID, gesture information, medical information obtaining condition, and medical information (actual data) shown in the medical information display apparatus 1 are data written into or read from a predetermined area of the main memory 16 or the auxiliary storage device 17 of the medical information display apparatus 1 by each of the processing units described above. In the mean time, the medical information management server 2 includes a medical information registration unit 51, a medical information retrieval unit 52, and a medical information database 53. The medical information registration condition, medical information, medical information obtaining condition, medical information (real data) shown in the medical information management server 2 are data written into or read from a predetermined area of the main memory or auxiliary storage device of the medical information management server 2, or an external storage device.

The medical information database 53 has a database structure in which patient ID, index information (to be described later in detail) corresponding to the medical information obtaining condition, and real data of the medical information are related.

The medical information registration unit 51 of the medical information management server 2 obtains medical information satisfying a predetermined medical information registration condition (to be described later in detail) from those generated in other systems (the electric medical record system 4, the image diagnostic system 5, the endoscopic examination system 6, the pathological examination system 7, and the each clinical department system 8) at a predetermined time interval, extracts patient ID and index information from the obtained medical information, converts the obtained medical information to the data structure of the medical information database 53, and registers the information in the medical information database 53. This causes display target medical information for the medical information display apparatus 1 to be accumulated in the medical information database 53.

Figure 5:
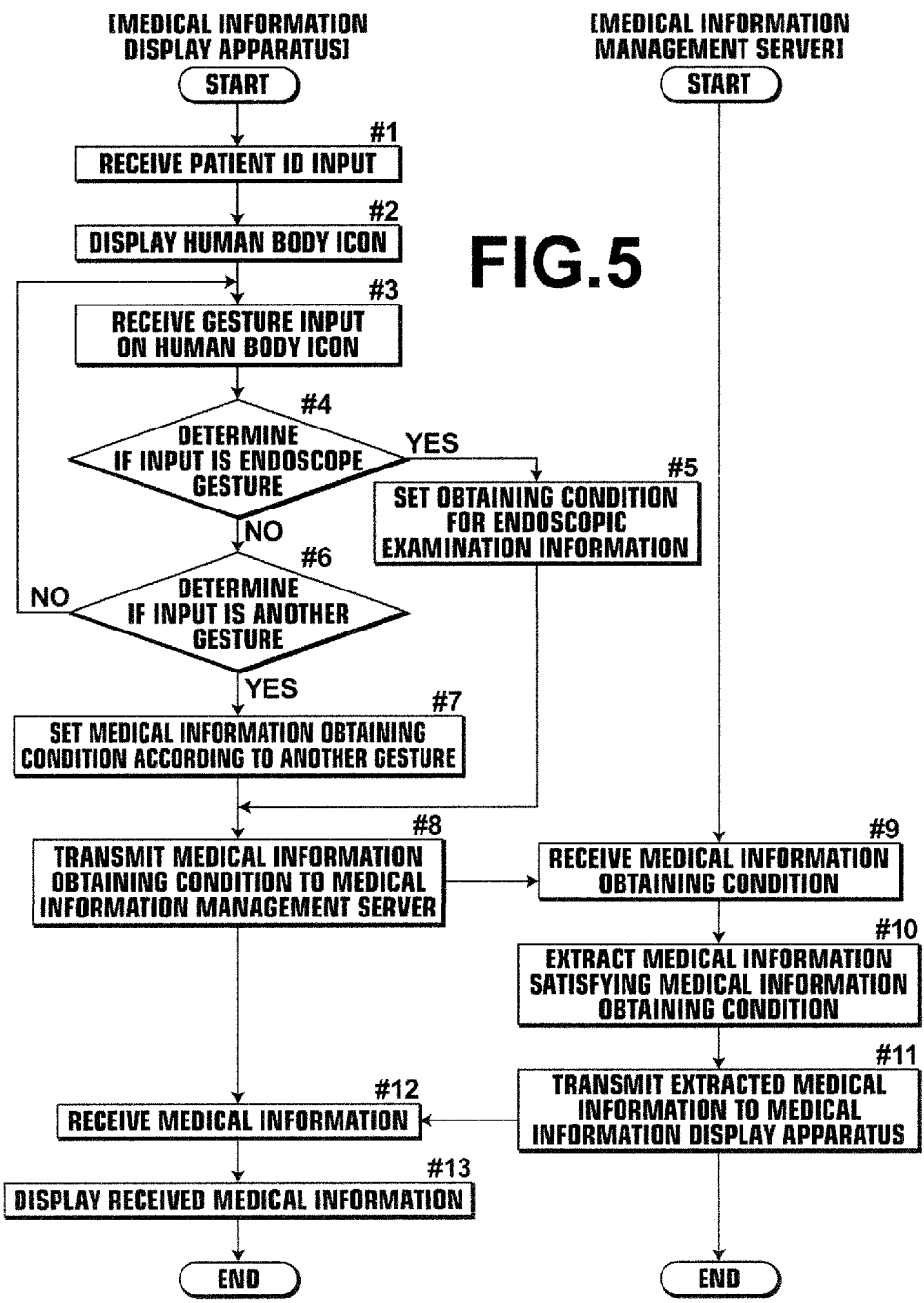
FIG. 5 is a flowchart illustrating a processing flow for displaying medical information performed in the medical information integration system in the first embodiment of the present invention.

FIG. 5 is a flowchart illustrating a processing flow for displaying medical information performed in the medical information integration system 3 in the first embodiment of the present invention. Steps from #1 to #8 and Steps from #12 to #13 are controlled by the main program of the application software executed in the medical information display apparatus 1. Hereinafter, an overall flow of the medical information display processing and individual steps performed by each processing unit of the medical information display apparatus 1 and medical information retrieval unit 52 of the medical information management server 2 will be described with reference mainly to FIGS. 4 and 5.

First, in the medical information display apparatus 1, the patient ID input UI 31 receives a patient ID and stores the inputted patient ID to a predetermined area of the main memory 16 (#1). More specifically, the patient ID is received, for example, using a software keyboard system in which an image of a keyboard or a numeric keypad is displayed on the liquid crystal display 12 and a key input displayed at the touched position on the touch panel 11 is received.

Figure 6:
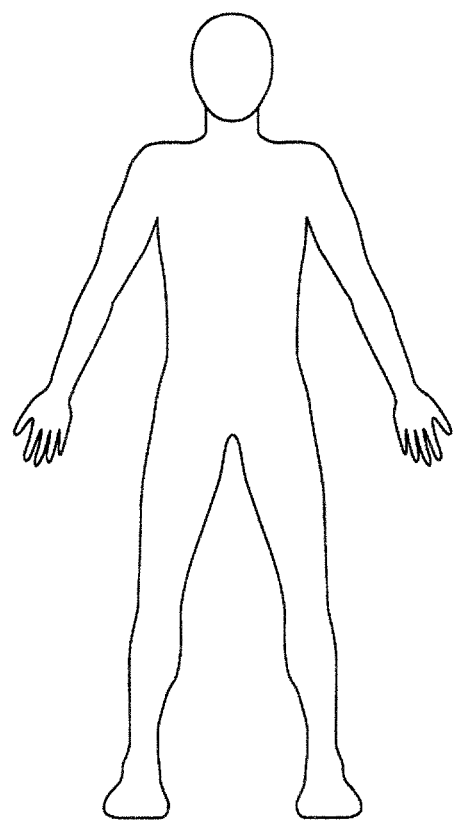
FIG. 6 illustrates, by way of example, a human body icon.

Next, the obtaining condition input UI 32 reads a human body icon image 45 from the auxiliary storage device 17, displays the icon at a predetermined display position on the liquid crystal display 12 (#2), receives gesture input of the user on the human body icon 45 from the touch panel 11, and stores the inputted gesture information in a predetermined area of the main memory 16 (#3). The human body icon 45 is a schematic representation of an entire human body, as illustrated, by way of example, in FIG. 6, and region information for identifying a region of a body is related to each position of a coordinate system of the human body icon 45. The gesture information represents information of a position in the coordinate system of the display device and information of each of the positions in the coordinate system of the display device corresponding to the trajectory of the gesture depicted on the touch panel 11 is outputted.

Processing from the next step, that is, from Step #4 to Step #7 are performed in the obtaining condition identification unit 33. Based on region information of the human body icon 45 and gesture information outputted from the obtaining condition input UI 32, the obtaining condition identification unit analyzes the gesture input inputted from the obtaining condition input UI 32 to identify a medical information obtaining condition for obtaining medical information of examination intuitively represented by the gesture. In the present embodiment, the obtaining condition identification unit 33 includes a plurality of individual condition identification units, each corresponding to each type of gesture input to be identified, and the endoscope condition identification unit 34 is one of them.

Based on gesture information and position information of the human body icon 45, the obtaining condition identification unit 33 first identifies at which position of the human body icon 45 the gesture input has been performed, as preprocessing common to the individual condition identification units. That is, the gesture information is position information in the coordinate system of the display device, while the region information of the human body icon 45 is related to the position information in the coordinate system of the human body icon 45, so that the obtaining condition identification unit 33 converts the information of both positions to position information in the same coordinate system using information of display position of the human body icon 45 in the coordinate system of the display device. This allows each of a plurality of points on the human body icon 45 forming the gesture input to be identified.

Next, based on the region information of the human body icon 45 and gesture information outputted from the obtaining condition input UT 32, the endoscope condition identification unit 34 of the obtaining condition identification unit 33 determines whether or not the gesture inputted through the obtaining condition input UI 32 is a gesture of inserting an endoscope into the human body represented by the human body icon 45 (endoscope gesture, FIGS. 9A, 9B) (#4). If the inputted gesture is determined to be an endoscope gesture (#4: YES), endoscope condition identification unit 34 stores a medical information obtaining condition (endoscope condition) in a predetermined area of the main memory 16 (#5). Specific endoscope gesture inputs and endoscope conditions will be described later in detail.

If the inputted gesture is determined not to be an endoscope gesture by the endoscope condition identification unit 34 (#4: NO), another condition identification unit (not shown) determines whether or not the inputted gesture is a predetermined gesture other than an endoscope gesture in a manner as in the endoscope condition identification unit 34 (#6). If the inputted gesture is determined to be the predetermined gesture (#6: YES), the another condition identification unit stores a medical information obtaining condition for obtaining medical information of examination corresponding to the predetermined gesture different from the endoscopic examination in a predetermined area of the main memory 16 (#7). On the other hand, if the inputted gesture is determined not to be a predetermined gesture (#6: NO), the processing returns to a waiting state for input of a new gesture from the obtaining condition input UT 32 (#3).

FIG. 5 indicates only two types of individual condition identification units, namely the endoscope condition identification unit and the other condition identification unit, but three or more individual condition identification units may be provided.

Next, the medical information obtaining unit 35 of the medical information display apparatus 1 transmits the medical information obtaining condition set by the obtaining condition identification unit 33 to the medical information management server 2 (#8). The medical information retrieval unit 52 of the medical information management server 2 receives the medical information obtaining condition from the medical information display apparatus 1 (#9), searches the medical information database 53 to extract real data of the medical information whose index information of the obtaining condition in the database satisfies the received medical information obtaining condition (#10), and transmits the extracted real data of the medical information to medical information display apparatus 1 (#11). The medical information obtaining unit 35 of the medical information display apparatus 1 receives the transmitted real data of the medical information and stores them in a predetermined area of the main memory 16 or in the auxiliary storage device 17 (#12). Then, the medical information display control unit 36 displays the medical information on the liquid crystal display 12 based on the received real data of the medical information (#13). If no medical information satisfying the medical information obtaining condition is registered in the medical information database 53, information notifying accordingly is displayed.

As described above, in the first embodiment of the present invention, when an endoscope gesture performed on the human body icon 45 is inputted from the touch panel 11 of the medical information display apparatus 1, endoscope related information is extracted from the medical information database 53 of the medical information management server 2 according to the endoscope gesture, and the extracted endoscope related information is displayed on the liquid crystal display 12 of the medical information display apparatus 1. Hereinafter, a series of specific processing steps for obtaining the endoscope related information will be described in detail. In the present embodiment, it is assumed that the endoscope related information includes virtual endoscopic images generated from three-dimensional volume data obtained by CT and the like and image interpretation reports with respect to the virtual endoscopic images, as well as real endoscopic images obtained through examinations using various types of endoscopes, reports of such examinations, and the like.

FIG. 7 illustrates a data structure of the medical information database 53 and specific examples of endoscope related information registered in the medical information database 53. As shown in the drawing, the medical information database 53 includes patient ID, index information corresponding to the medical information obtaining condition, and real data. The index information includes a gesture type index for identifying the gesture type for which the medical information should be obtained and a gesture region index representing a region identified by the gesture for which the medical information should be obtained. Accordingly, the medical information obtaining condition also includes a gesture type condition representing the gesture type index condition of obtaining target medical information and a gesture region condition representing a gesture region index condition.

The medical information registration condition for registering medical information in the medical information database 53 is defined in advance for each collecting source system or database of medical information. The medical information registration condition of endoscope related information extracted according to an endoscope gesture may include the following three conditions: all sets of information in the endoscopic examination database of the endoscopic examination system 6 (Condition No. 1); information having auxiliary information indicating a virtual endoscopic image for the image database of the image diagnostic system 5 (Condition No. 2); and information related to image ID of a virtual endoscopic image stored in the image database for the image interpretation report database of the image diagnostic system 5 (Condition No. 3), as summarized in FIG. 8. These medical information registration conditions may be defined as reference data or implemented as a subprogram with respect to each registration condition.

The medical information registration unit 51 collects medical information that satisfies one of the three medical information registration conditions from each system and creates registration data to be registered in the medical information database 53 using the collected medical information. More specifically, a patient ID is extracted from each of the collected medical information and set to the entry of patient ID of the medical information database 53. Information representing an endoscope gesture (character string, code, or the like; "endoscope" is used here) is set to the entry of gesture type index of the index information. Region information of a patient is extracted from auxiliary information of corrected medical information and the like and set to the entry of gesture region index. Real data of the collected medical information are set to the entry of real data. Then, the created registration data are registered (inserted) in the medical information database 53. In the specific examples of FIG. 7, the registration data of information Nos. 1, 2, 4, and 5 are those registered based on the medical information registration condition of Condition No. 1 in FIG. 8, the registration data of information Nos. 3 and 6 are those registered based on the medical information registration condition of Condition No. 2, and the registration data of Information No. 7 are those registered based on the medical information registration condition of Condition No. 3 in FIG. 8.

Figure 9A:
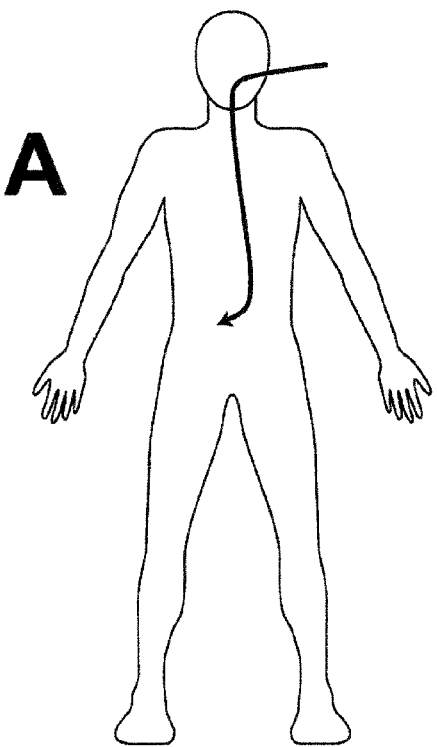
FIG. 9A illustrates, by way of example, a gesture of inserting an upper gastrointestinal endoscope into a human body represented by a human body icon.
Figure 9B:
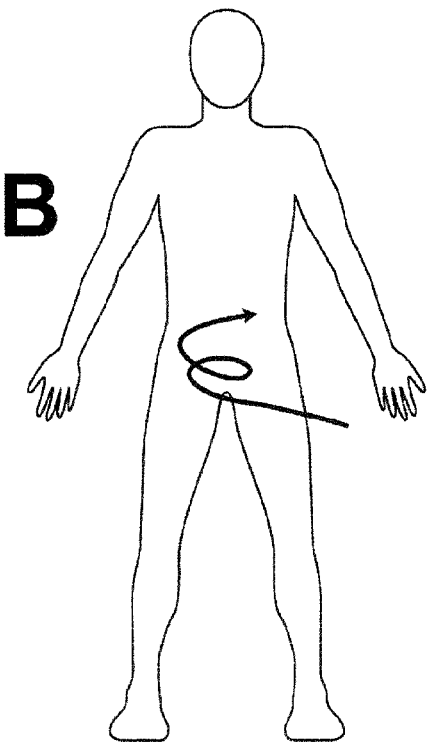
FIG. 9B illustrates, by way of example, a gesture of inserting a large intestine endoscope into the human body represented by the human body icon.

The obtaining condition input UT 32 receives inputs of endoscope gestures like those illustrated, by way of example, in FIGS. 9A and 9B, and outputs gesture information thereof. FIG. 9A illustrates an example of gesture input representing an insertion operation of an upper gastrointestinal endoscope in which the arrow indicates a gesture depicting a trajectory from the mouth or nose of the human body icon 45, through esophagus, to the stomach or duodenum. FIG. 9B illustrates an example of gesture input representing an insertion operation of a large intestine endoscope in which the arrow indicates a gesture depicting a trajectory from the position of the anus of the human body icon 45 to near the rectum or colon.

The endoscope condition identification unit 34 determines whether or not the inputted gesture is an endoscope gesture, and if it is determined to be an endoscope gesture, outputs a medical information obtaining condition for obtaining endoscope related information corresponding to the gesture. Here, reference data in which information representing a plurality of endoscope gesture patterns and information set to the region of medical information obtaining condition, as required, with respect to each endoscope gesture pattern are defined is used in determining an endoscope gesture.

FIG. 10A illustrates a first example of the reference data in which a combination of regions of start and end points of a gesture is defined as the reference data representing an endoscope gesture. That is, the endoscope condition identification unit 34 identifies to which regions of the human body icon 45 the start and end points of the inputted gesture belong and, if the identified combination of regions of the start and end points is one of the combinations defined in the reference data, determines that the inputted gesture is an endoscope gesture. Here, if the start point of the inputted gesture is outside of the human body icon 45, a region of the human body icon 45 nearest to the start point or a region related to the position where the trajectory of the inputted gesture first intersects (contacts) the human body icon 45 when the trajectory is traced from the start point of the gesture may be regarded as the start point region. In the example shown in FIG. 10A, the reference data are defined such that the inputted gesture is determined to be an endoscope gesture if the start point region of the inputted gesture is either the mouth or nose and the end point region is one of the esophagus, stomach, duodenum, small intestine, trachea, and tracheal branch, or if the start point region is the anus and the end point region is either the large or small intestine. Then, if the inputted gesture is determined to be an endoscope gesture, the endoscope condition identification unit 34 outputs a medical information obtaining condition in which the gesture type is set as "endoscope" and the gesture region is set to the end point region of the gesture. For example, if the gesture shown in FIG. 9A is inputted, the gesture region of the medical information obtaining condition is "stomach" while if the gesture shown in FIG. 9B is inputted, the gesture region of the medical information obtaining condition is "large intestine".

In the first example described above, as no consideration is given to the trajectory between the start and end points, even a gesture depicting, for example, a trajectory of mouth→esophagus→trachea→tracheal branch→lung→stomach→esophagus is determined to be an endoscope gesture.

Consequently, in a second example of reference data shown in FIG. 10B, a change pattern of regions of the human body icon 45 on the trajectory of a gesture arranged in the order in which the trajectory has passed between the start to end points of the gesture is defined as the reference data. The endoscope condition identification unit 34 sequentially traces each point on a trajectory of an inputted gesture from the start point to identify a region at each point, thereby identifying a change pattern of the regions on the trajectory of the inputted gesture. Then, if the identified region change pattern corresponds to a pattern defined in the reference data, the gesture is determined to be an endoscope gesture. Thus, if a gesture depicting, for example, a trajectory that passes in the order of mouth or nose→esophagus is inputted, the gesture is determined to be an endoscope gesture. On the other hand, if a gesture depicting a trajectory that passes mouth→esophagus→trachea→tracheal branch→lung→stomach→esophagus as described above is inputted, the gesture is not determined to be an endoscope gesture. If the inputted gesture is determined to be an endoscope gesture, the endoscope condition identification unit 34 outputs a medical information obtaining condition in which the gesture type is set as "endoscope" and the gesture region is set to the end point region of the gesture.

In the second example described above, a determination is made as to whether or not an inputted gesture is an endoscope gesture using regions of the human body icon 45 on which the trajectory of the inputted gesture has passed, but a determination may be made as to whether or not an inputted gesture is an endoscope gesture in view of the depicted direction or shape of the trajectory of the inputted gesture.

Figure 11A:
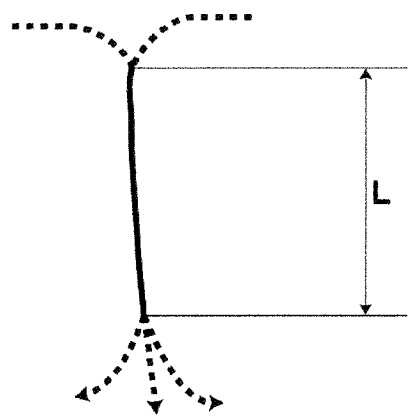
FIG. 11A schematically illustrates, by way of example, a trajectory shape model of endoscope gesture.
Figure 11B:
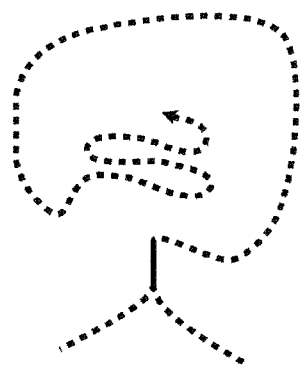
FIG. 11B schematically illustrates, by way of example, another trajectory shape model of endoscope gesture.

FIG. 10C shows a third example of reference data, in which a combination of shape model of trajectory and end point region is used as reference data. In the example, two types of trajectory shape models are provided by classifying trajectory shapes of endoscope gestures into a trajectory shape of oral or nasal endoscope in which an endoscope is inserted from mouth or nose and a trajectory shape of transanal endoscope in which an endoscope is inserted from anal. FIG. 11A schematically illustrates a trajectory shape model of oral/nasal endoscope (Model 01). As illustrated in the drawing, Model 01 represents a shape of a trajectory that moves downward from left or right by curving downward and includes any one of the portions that curve left, curve right, and move straight downward near the end point of the trajectory with the length of trajectory section moving straight downward (section indicated by "L" in the drawing) being set to an arbitrary value. FIG. 11B schematically illustrates a trajectory shape model of transanal endoscope (Model 02). As illustrated in the drawing, Model 02 represents a shape of a trajectory that moves upward from left or right by curving upward without any restriction on the shape after moved upward. These shape models define the directions into which the trajectories are depicted and relative positional relationship between each of a plurality of points forming the trajectory and does not include information of a position on the human body icon 45. Consequently, in a third example, the endoscope condition identification unit 34 determines an inputted gesture to be an endoscope gesture if the shape of the inputted gesture corresponds to either one of the two shape models described above and the end point region of the gesture corresponds to an end point region related to the trajectory shape model in the reference data by further using end point region information. For example, if the shape of an inputted gesture corresponds to the trajectory shape model of oral/nasal endoscope and the end point region of the gesture is stomach, the gesture is determined to be an endoscope gesture. On the other hand, even in the case where the shape of an inputted gesture corresponds to the trajectory shape model of oral/nasal endoscope, if the end point region is large intestine, the gesture is not determined to be an endoscope gesture because no oral/nasal large intestine endoscope exits and no combination of such trajectory model and end point region is defined in the reference data. In the third example also, if the inputted gesture is determined to be an endoscope gesture, the endoscope condition identification unit 34 outputs a medical information obtaining condition in which the gesture type is set as "endoscope" and the gesture region is set to the end point region of the gesture. The determination as to whether or not an inputted gesture matches a trajectory shape model may be made by calculating a degree of agreement (similarity) between a characteristic amount of the inputted gesture and that of the trajectory model by any known pattern recognition technology used for character recognition and fingerprint authentication, and if the calculated degree of agreement (similarity) is greater than or equal to a predetermined threshold value, they can be said to be matched (as described, for example, in Japanese Unexamined Patent Publication No. 8 (1996)-083318).

The three examples described above are based on the assumption that region information is related to each position of the human body icon 45 but, instead, reference data in which region names of FIGS. 10A to 10C are replaced with information representing a range of coordinate values in which each region can exist may be used. FIG. 10D shows a fourth example of reference data and illustrates the case in which change patterns of regions on the trajectories of the reference data of FIG. 10B are represented by coordinate value ranges. In this case, the endoscope condition identification unit 34, for example, sequentially searches for each point on the trajectory of an inputted gesture from the start point of the gesture, and if the coordinate value changes from a value in a coordinate value range corresponding to mouth or nose to a value in a coordinate value range corresponding to esophagus and the search point reaches the end point of the gesture in the coordinate value range corresponding to esophagus, determines the gesture to be an endoscope gesture. In this case, since region information is not related to each position of the human body icon 45, it can not be recognized that the position of the end point of the gesture is in a portion of esophagus. Consequently, in this case, it is necessary to relate an end point region of gesture, i.e., region information of the medical information obtaining condition to a change pattern of coordinate value ranges on each trajectory in the reference data. When an inputted gesture is determined to be an endoscope gesture, this allows the endoscope condition identification unit 34 to set the gesture type of a medical information obtaining condition as "endoscope", then to obtain gesture region information of a medical information obtaining condition related to a change pattern of the coordinate value ranges on the trajectory of the endoscope gesture from the reference data, as the gesture region of a medical information obtaining condition, and to output a medical information obtaining condition corresponding to the inputted gesture. Also for FIGS. 10A and 10C, the start point region and end point region of a gesture may be defined by coordinate value ranges and reference data in which information of regions of medical information obtaining conditions are related may be used in the same manner as described above.

FIG. 10E shows a fifth example of reference data used for determining an endoscope gesture in which trajectory shape/position models are listed, each being modeled by a trajectory shape in conjunction with a position on the human body icon 45. That is, trajectory shape/position models can be said that FIGS. 9A and 9B are directly modeled. For example, the trajectory shape/position model corresponding to FIG. 9A may become a model representing a trajectory that enters the mouth or nose of the human body icon 45 from left or right, curves downward to passes through the esophagus and reaches the stomach. The modeling in the manner described above requires models according to the endoscope type and position reached as shown, by way of example, in the trajectory shape/position models listed in FIG. 10E. The endoscope condition identification unit 34 determines an inputted gesture to be an endoscope gesture if the shape and position of the inputted gesture matches any one of the trajectory shape/position model shown in FIG. 10E. For the determination, any known pattern recognition technology may be used, as in the third example. Further, in this example, when determining whether or not a gesture is an endoscope gesture, an end point region is not identified and instead region information of medical information obtaining condition is related to each trajectory shape/position model in the reference data. Therefore, when an inputted gesture is determined to be an endoscope gesture, the endoscope condition identification unit 34 obtains a region related to the trajectory shape/position model that matches the inputted gesture from the reference data, sets the gesture type as "endoscope", and outputs a medical information obtaining condition with the gesture region being as the obtained region. Note that an arrangement may be adopted in which the reference data do not include region information of medical information obtaining condition, and a region of the human body icon 45 corresponding to the end point of the inputted gesture is identified when a medical information obtaining condition is outputted and the identified region is outputted as the region information of the medical information obtaining condition.

Further, in the example of FIG. 10E, an increased number of models are required since one model includes not only shape information but also position information. Consequently, an arrangement may be adopted in which a start point region of a gesture is included in the reference data, and the endoscope condition identification unit 34 identifies a start point region of an inputted gesture prior to performing pattern recognition and pattern recognition is performed only for the trajectory shape/position models related to the region in the reference data, as shown in FIG. 10F. For example, in the case where the start point region of an inputted gesture is mouth and the reference data are those shown in FIG. 10F, pattern recognition may be performed only for Models 11 to 16 whose start point region is mouth, while if the start point region of an inputted gesture is anus, the pattern recognition may be performed only for Models 17 and 18 whose start point region is anus in the reference data of FIG. 10F. As described above, inclusion of information of the start point regions of gestures in the reference data allows the number of trajectory shape/position models that require pattern recognition using the start point region of an inputted gesture to be reduced, whereby processing load may be reduced.

The medical information retrieval unit 52 of the medical information management server 2 receives the medical information obtaining condition set in the manner described above from the medical information obtaining unit 35 of the medical information display apparatus 1 and extracts medical information satisfying the received medical information obtaining condition, that is, endoscope related information from the medical information database 53. For example, in the case where the medical information shown in FIG. 7 is stored in the medical information database 53 and an endoscope gesture shown in FIG. 9A is inputted, as well as "012345" as the patient ID, in the medical information display apparatus 1, then the following are set to the medical information obtaining condition: "012345" as the patient ID, "endoscope" as the gesture type, and "stomach" as the gesture region and the medical information obtaining condition is transmitted to the medical information management server 2. Here, the medical information retrieval unit 52 extracts medical information of Information No. 1 whose index information satisfies the medical information obtaining condition and transmits the extracted information to the medical information display apparatus 1. In the mean time, in the case where the aforementioned patient ID and the endoscope gesture shown in FIG. 9B are inputted, the following are set to the medical information obtaining condition: "012345" as the patient ID, "endoscope" as the gesture type, and "large intestine" as the gesture region and the medical information obtaining condition is transmitted to the medical information management server 2. Here, the medical information retrieval unit 52 extracts medical information of Information No. 3 whose index information satisfies the medical information obtaining condition and transmits the extracted information to the medical information display apparatus 1. In the medical information display apparatus 1, the medical information obtaining unit 35 obtains the transmitted medical information and the medical information display control unit 36 displays the obtained medical information on the liquid crystal display 12.

As described above, according to the first embodiment of the present invention, the endoscope condition identification unit 34 may recognize an extremely intuitive and simple gesture operation inputted from the touch panel 11 by way of the obtaining condition input UI 32 and representing an endoscope operation. Then, in the case where the gesture representing the endoscope operation is recognized, the medical information obtaining unit 35 may obtain endoscope related information from medical information database 53 of the medical information management server 2, and medical information display control unit 36 may display the obtained endoscope related information on the liquid crystal display 12. Thus, the user may display endoscope related information of a desired region only by a single action of performing an endoscope gesture operation on the touch panel 11 of the medical information display apparatus 1. Here, for example, even when a virtual endoscopic image and a cross-sectional image representing the same region are registered in the medical information database 53, the virtual endoscopic image is displayed. In this way, the medical information display apparatus 1 of the present invention has extremely high operability and a high practical value.

In the case of the first embodiment, the obtaining condition identification unit 33 analyzes an inputted gesture to identify the medical information obtaining condition first and then processing for obtaining medical information from the medical information management server 2 is performed. This may result in a prolonged wait time for the user of the medical information display apparatus 1 from the completion of the gesture to the display of the medical information, whereby the operability may be degraded.

Consequently, in a second embodiment of the present invention, while receiving gesture input after receiving a patient ID, medical information according to the inputted patient ID is to be obtained in advance in the background.

Figure 13:
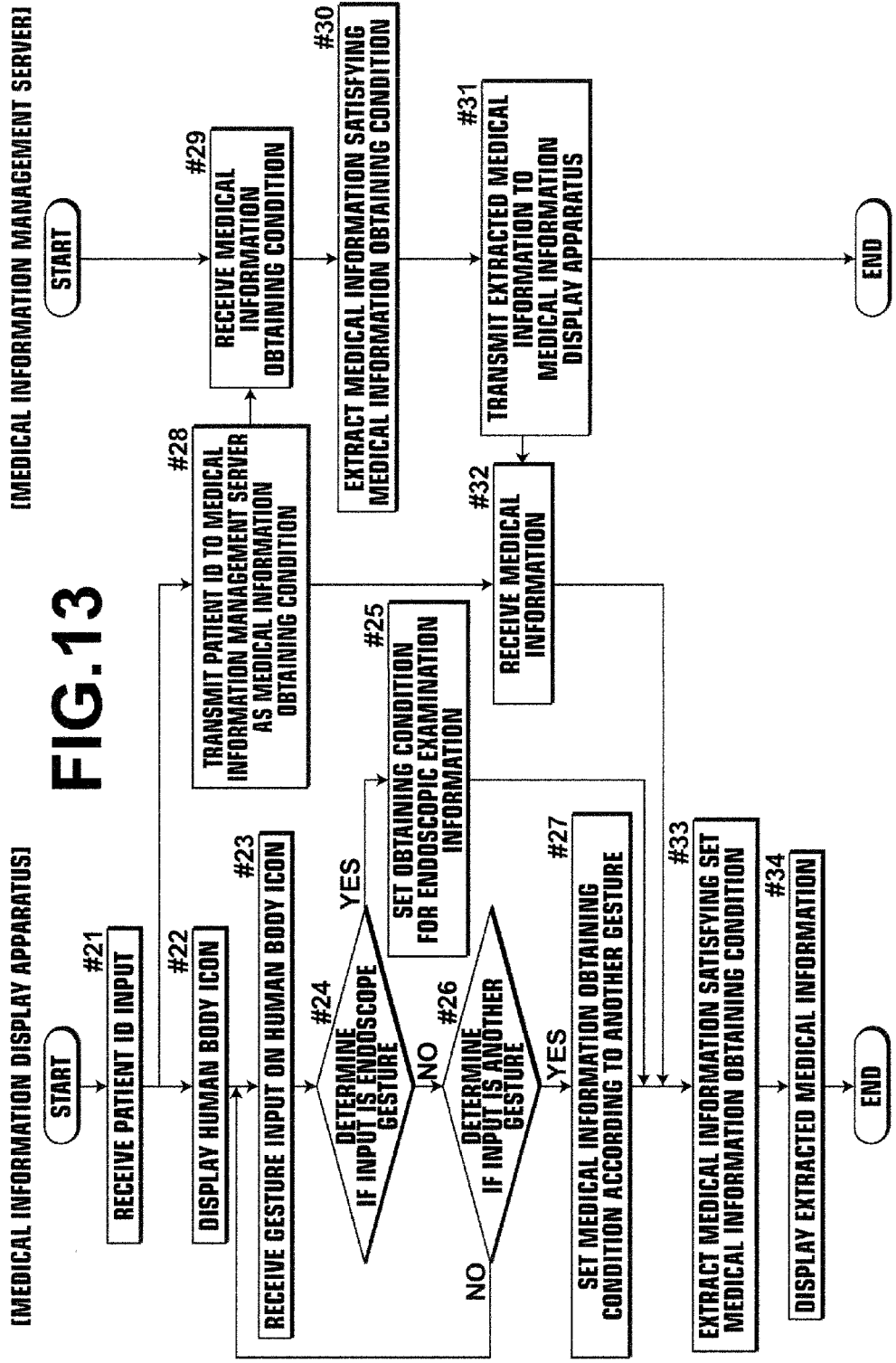
FIG. 13 is a flowchart illustrating a processing flow for displaying medical information performed in the medical information integration system in the second embodiment of the present invention.

FIG. 12 is a functional block diagram of a medical information display apparatus 1 and a medical information management server 2 according to a second embodiment of the present invention. As illustrated in the drawing, the present embodiment is of a configuration in which a medical information pre-obtaining unit 37 is added to the medical information display apparatus 1 of the first embodiment and the medical information obtaining unit 35 of the first embodiment is replaced with a medical information extraction unit 38. FIG. 13 is a flowchart illustrating a processing flow for displaying medical information performed in the medical information integration system 3 in the second embodiment of the present invention.

As shown in the drawing, after input of a patient ID is received by the patient ID input UI 31 as in the first embodiment (#21), the medical information pre-obtaining unit 37 transmits a medical information obtaining condition, in which only the inputted patient ID is set, to the medical information management server 2 as background processing (#28). The medical information retrieval unit 52 of the medical information management server 2 receives the medical information obtaining condition (only the patient ID) (#29), then searches the medical information database 53, and extracts medical information with a patient ID that matches the patient ID of the received medical information obtaining condition in the database (#30). Here, not only real data of the medical information but also index information corresponding to the medical information obtaining condition is extracted. The medical information retrieval unit 52 transmits the extracted medical information to the medical information display apparatus 1 (#31). The medical information pre-obtaining unit 37 of the medical information display apparatus 1 receives the transmitted medical information and stores the information in a predetermined area of the auxiliary storage device 17 or main memory 16 (#32).

In the mean time, while the processing described above is performed by the medical information pre-obtaining unit 37, steps of receiving gesture input and setting a medical information obtaining condition according to the gesture are performed (#22 to #27) in the medical information display apparatus 1, as in Steps #2 to #7 of the first embodiment.

Based on the medical information obtaining condition set according to the inputted gesture and the index information of the medical information obtained by the medical information pre-obtaining unit 37, medical information satisfying the medical information obtaining condition is extracted from the pre-obtained medical information by the medical information extraction unit 38 (#33). Then, based on real data of the extracted medical information, the medical information display control unit 36 displays the medical information on the liquid crystal display 12 (#34).

As described above, in the second embodiment of the present invention, medical information pre-obtaining unit 37 pre-obtains medical information related to the patient ID inputted through the patient ID input UI 31 from the medical information database 53 of the medical information management server 2 in parallel with the step of receiving gesture input by the obtaining condition input UI 32 and the step of identifying a medical information obtaining condition by obtaining condition identification unit 33 in the medical information display apparatus 1. When obtaining medical information satisfying the medical information obtaining condition according to the inputted gesture, this eliminates the need to gain access to the medical information database 53 of the medical information management server 2. This eliminates the need for the user of the medical information display apparatus 1 to wait for the retrieval operation performed by the medical information management server 2 and communication between the medical information display apparatus 1 and medical information management server 2, therefore, a throughput from the viewpoint of the user is improved and the operability is enhanced. Even when the medical information management server 2 and the network 9 have high loads or low performance, this embodiment may alleviate the influence thereof by pre-obtaining medical information.

A third embodiment of the present invention is to improve the operability in the case where a plurality of sets of medical information satisfying the medical information obtaining condition is extracted.

Figure 14:
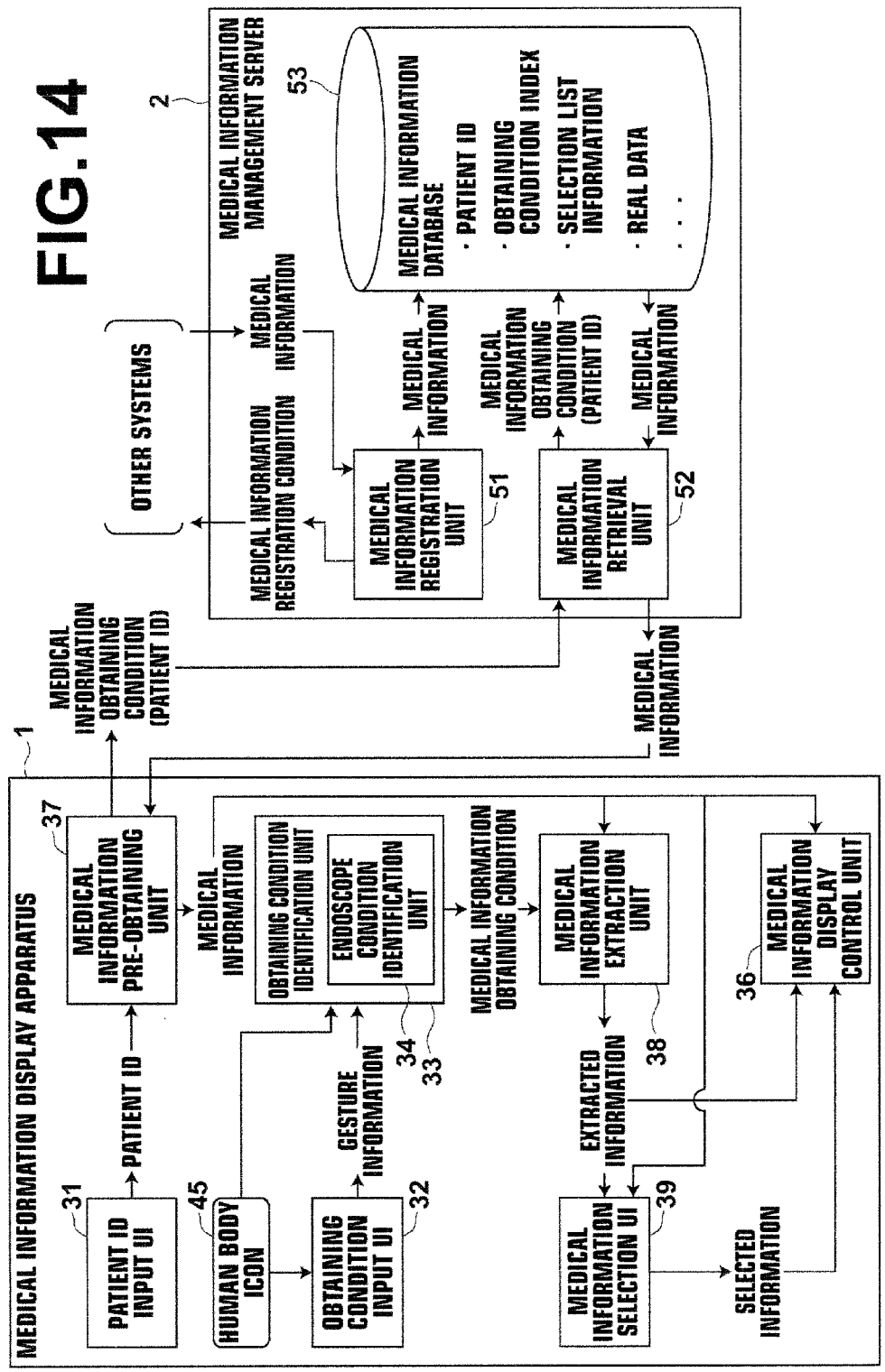
FIG. 14 is a block diagram of the medical information display apparatus and medical information management server, schematically illustrating the functions implemented therein in a third embodiment.

FIG. 14 is a functional block diagram of a medical information display apparatus 1 and a medical information management server 2 according to the third embodiment of the present invention. As illustrated in the drawing, the present embodiment is of a configuration in which a medical information selection UI 39 is added to the medical information display apparatus 1 of the second embodiment described above. Further, the medical information database 53 is of a data structure in which selection list information is added to the data structure of the first embodiment, as further detailed in FIG. 16. In the example shown in FIG. 16, the selection list information includes date and time of examination, examination type, and information type. These items of information may be extracted by the medical information registration unit 51 from the name of the source system or the name of the source database of the registration target medical information, auxiliary information of the registration target medical information, and the like.

FIGS. 15A and 15B show a flowchart illustrating a processing flow for displaying medical information performed in the medical information integration system 3 in the third embodiment of the present invention. As illustrated in the drawings, Steps #41 to #53 are identical to Steps #21 to #33 in the second embodiment.

Figure 17B:
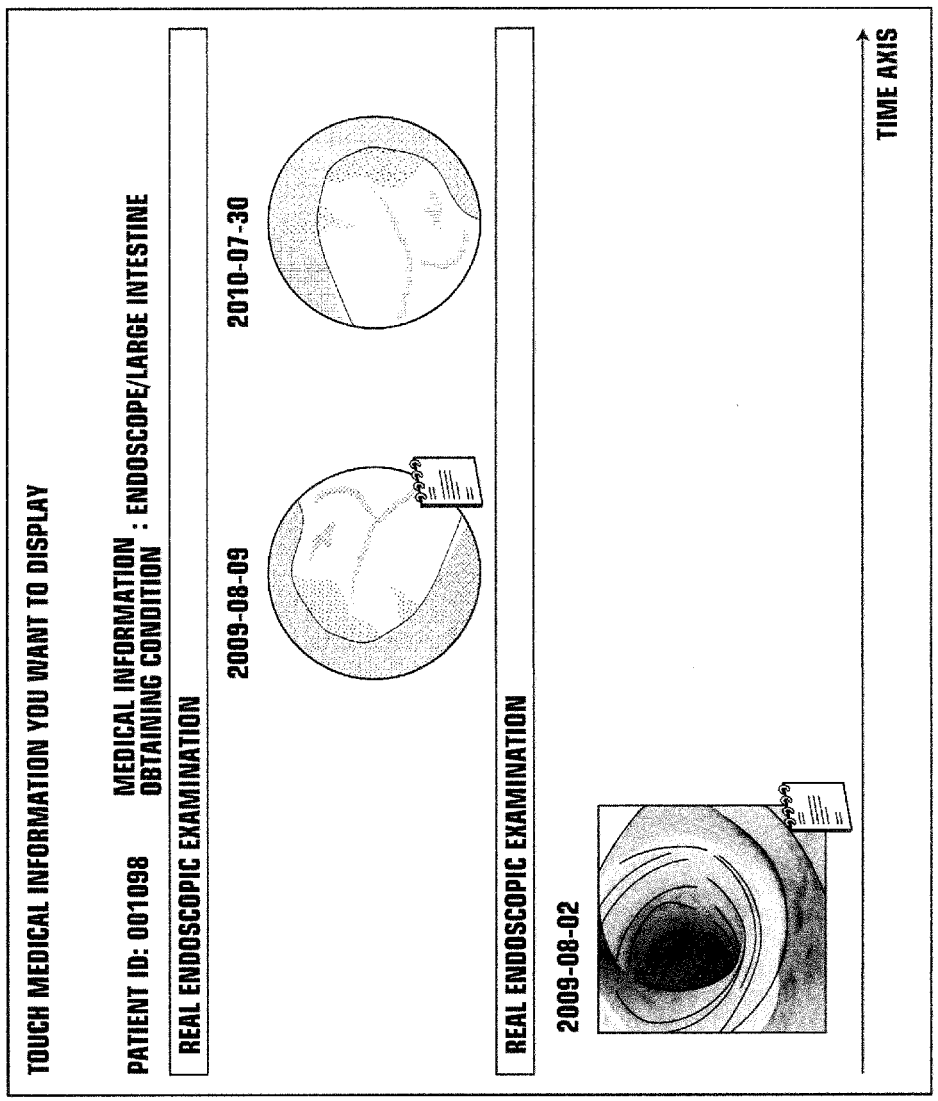
FIG. 17B illustrates, by way of example, an alternative medical information selection screen.

In Step #53, if only one set of medical information satisfying the medical information obtaining condition is extracted by the medical information extraction unit 38 (#54; NO), the medical information display control unit 36 displays the extracted medical information on the liquid crystal display 12 based on real data of the medical information (#57). On the other hand, if a plurality of sets of medical information is extracted by the medical information extraction unit 38 (#54; YES), the medical information selection UI 39 displays a medical information selection screen on the liquid crystal display 12 (#55). FIG. 17A illustrates, by way of example, a medical information selection screen. The screen shows the case in which sets of medical information satisfying the patient ID="001098" are obtained from the medical information database 53 illustrated, by way of example, in FIG. 16 by the medical information pre-obtaining unit 37 and sets of medical information satisfying the gesture type="endoscope" and the gesture region="large intestine" are extracted by the medical information extraction unit 38. The medical information selection UI 39 displays a list of the extracted sets of medical information for selection. Then, the medical information selection UI 39 receives the selection of a row representing medical information desired by the user (#56). FIG. 17B illustrates, by way of example, a visually more effective medical information selection screen. As illustrated in the drawing, medical information whose information type is image is displayed as a thumbnail with respect to each examination type in the medical information selection screen. Further, medical information whose information type is report is displayed as an icon representing the report at the lower right of the medical information (image) related to the target of the report. Still further, each set of medical information is arranged with the horizontal axis direction as the time axis based on information of examination date and time of the selection list information. In the example screen, the medical information selection UI 39 receives selection (touch operation) of a thumbnail image representing medical information or an icon desired by the user. Then, the medical information display control unit 36 displays the selected medical information on the liquid crystal display 12 based on real data of the medical information (#57).

As described above, in the third embodiment of the present invention, if a plurality of sets of medical information satisfying the medical information obtaining condition identified by the obtaining condition identification unit 33 is extracted by the medical information extraction unit 38 of the medical information display apparatus 1, the medical information selection UI 39 receives selection of medical information to be displayed, so that the user may display desired medical information by a simple touch operation, whereby the operability is further enhanced.

In each of the aforementioned embodiments, a virtual endoscopic image previously generated by the image diagnostic system 5 is used as medical information. In contrast, a fourth embodiment of the present invention is to display endoscope related medical information more interactively.

FIG. 18 is a functional block diagram of a medical information display apparatus 1 and a medical information management server 2 according to the fourth embodiment of the present invention. As illustrated in the drawing, the present embodiment is of a configuration in which an endoscopic image display mode selection UI 40 and a virtual endoscopic image generation unit 41 are added to the medical information display apparatus 1 of the third embodiment described above.

Further, the medical information database 53 is of a data structure in which the examination type of the selection list information in the data structure of the third embodiment is replaced with modality type, as detailed in FIG. 20. The entry of the modality type includes a modality type representing the modality that has obtained the medical information (image). These modality types may be extracted by the medical information registration unit 51 from the name of the source system or the name of the source database of the registration target medical information, auxiliary information of the registration target medical information, and the like. In the present embodiment, volume data (CT image in the drawing) obtained by CT are stored as real data of medical information instead of a virtual endoscopic image. That is, in the present embodiment, medical information registration unit 51 registers medical information with auxiliary information signifying a CT image, instead of Condition No. 2 in FIG. 8, in the image database of the image diagnostic system 5. Further, in the present embodiment, it is assumed that medical information representing a real endoscopic image includes auxiliary information representing the position of the patient and imaging direction of the real endoscopic image.

FIGS. 19A and 19B show a flowchart illustrating a processing flow for displaying medical information performed in the medical information integration system 3 in the fourth embodiment of the present invention. As illustrated in the drawings, Steps #61 to #74, #83 and #84 are identical to Steps #41 to #54, #55 and #56 in the third embodiment.

If a plurality of sets of medical information is extracted by the medical information extraction unit 38 (#74; YES), and if a gesture inputted through the obtaining condition input UI 32 is an endoscopic image and a CT image is included in the sets of medical information extracted by the medical information extraction unit 38 (if medical information with the modality type "CT" and information type "image" in the selection list information is present) (#75; YES), the medical information selection UI 39 and the endoscopic image display mode selection UI display a medical information selection/endoscopic image display mode selection screen on the liquid crystal display 12 (#76). FIG. 21 illustrates, by way of example, a medical information selection/endoscopic image display mode selection screen. As illustrated in the drawing, the example screen is of a configuration in which a check box of "simultaneous display of real and virtual endoscopic images" for receiving endoscopic image display mode is added to the example screen in FIG. 17A at the bottom. The medical information selection/endoscopic image display mode selection screen may be, for example, the example screen in FIG. 17B with the check box for receiving selection of endoscopic image display mode described above.

Then, as in the third embodiment, the medical information selection UI 39 receives selection (touch operation) of a row representing medical information desired by the user and endoscopic image display mode selection UI 40 receives selection (touch operation on the check box) of endoscopic image display mode desired by the user (#77).

If medical information representing a. CT image is not selected (#78; NO), the medical information display control unit 36 displays medical information selected through the medical information selection UI 39 on the liquid crystal display 12 based on real data of the medical information, as in the third embodiment (#85). In contrast, if the medical information representing a CT image is selected (#78; YES), a determination is made as to whether or not selection of simultaneous display of real and virtual endoscopic images is received by the endoscopic image display mode selection UI 40.

As a result of the determination, if the simultaneous display is not selected (#79; NO), the virtual endoscopic image generation unit 41 generates a virtual endoscopic image from the CT image which is the medical information selected through the medical information selection UI 39 based on a predetermined image generation condition (#82). Then, the medical information display control unit 36 displays the generated virtual endoscopic image on the liquid crystal display 12 (#85). Here, an arrangement may be adopted in which a user interface for receiving setting of generation conditions (position, imaging direction, color template, and the like) of a virtual endoscopic image and a virtual endoscopic image is generated based on the determined generation conditions.

In the mean time, if the simultaneous display is selected (#79; YES), the virtual endoscopic image generation unit 41 obtains, from real data of medical information representing the real endoscopic image selected through the medical information selection UT 39, auxiliary information representing the position of the patient of the real endoscopic image and imaging direction, and identifies the position and imaging direction in the CT image (#80). The virtual endoscopic image generation unit 41 generates a virtual endoscopic image from the CT image selected through the medical information selection UI 39 based on the identified position and imaging direction (#81). Then, the medical information display control unit 36 simultaneously displays the real endoscopic image selected through the medical information selection UI 39 and the virtual endoscopic image generated by the virtual endoscopic image generation unit 41 on the liquid crystal display 12 (#85).

The virtual endoscopic image generation unit 41 generates the virtual endoscopic image by setting a given position as a viewpoint, setting a plurality of visual lines radially extending from the viewpoint within a given range of field angle such that a given imaging direction corresponds to the central direction of the field, and projecting pixel values on each visual line by volume rendering based on the known central projection.

As the specific example methods for relating the positions and imaging directions between the real endoscopic image and virtual endoscopic image (CT image), the following may be cited. In the case where the position within the patient at which a real endoscopic image is obtained is represented by the length from the endoscope insertion position on the endoscope path, virtual endoscopic image generation unit 41 may first detect the endoscope insertion path (e.g., in the case of large intestine, core line of large intestine) and a position corresponding to the real endoscope insertion position from the CT image by a known image recognition algorithm. Then, a position advanced from the position corresponding to the real endoscope insertion position by a length on the endoscope insertion path in the CT image corresponding to the length from the real endoscope insertion position to the position at which the real endoscope image has been obtained and the obtained position may be determined to the position at which the virtual endoscopic image is to be generated. Otherwise, in the case where the relationship between the coordinate system at the time of the real endoscopic examination and the coordinate system of the CT image is known, the position in the CT image corresponding to the position at which the real endoscope image has been obtained, i.e., the position at which the virtual endoscopic image is to be generated may be calculated by the coordinate conversion based on the relationship (as described, for example, in Japanese Unexamined Patent Publication No. 2006-198032).

Figure 22A:
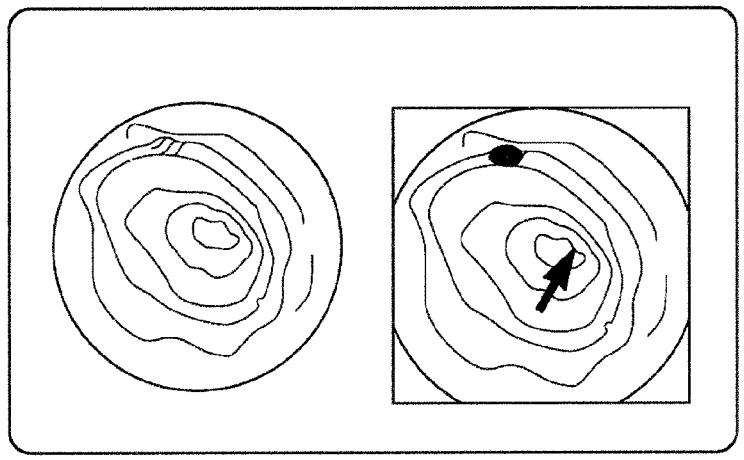
FIG. 22A illustrates a first specific example of simultaneous display of real endoscopic image and virtual endoscopic image.
Figure 22B:
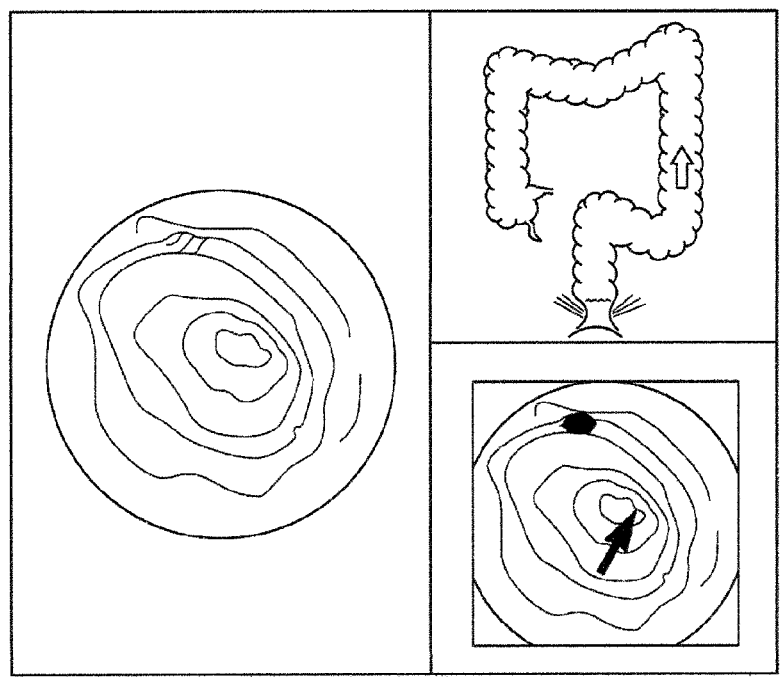
FIG. 22B illustrates a second specific example of simultaneous display of real endoscopic image and virtual endoscopic image.
Figure 22C:
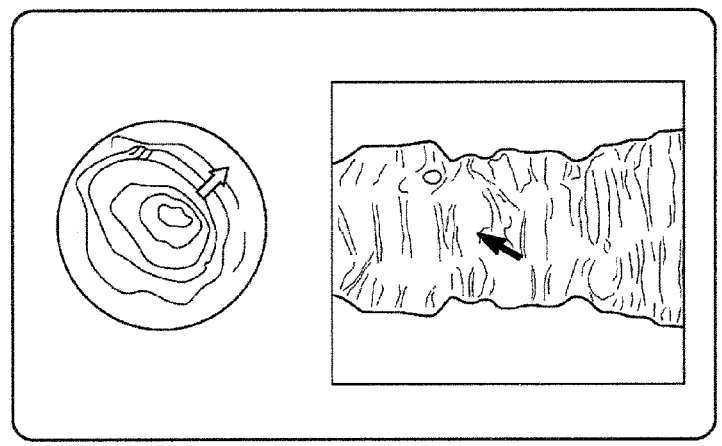
FIG. 22C illustrates a third specific example of simultaneous display of real endoscopic image and virtual endoscopic image.
Figure 22D:
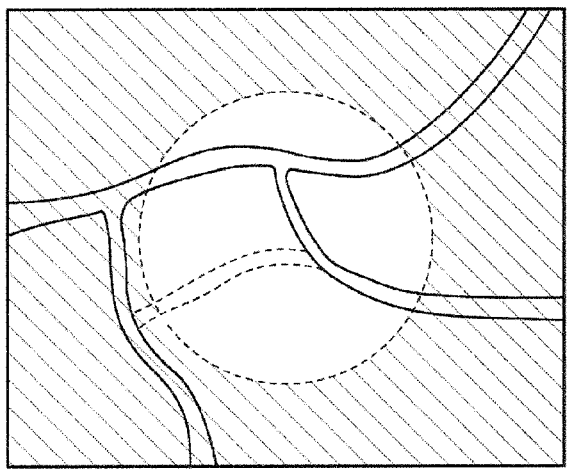
FIG. 22D illustrates a fourth specific example of simultaneous display of real endoscopic image and virtual endoscopic image.

FIGS. 22A to 22D illustrate specific examples of simultaneous display of real and virtual endoscopic images. FIG. 22A shows an example in which a real endoscope image (left) and a virtual endoscopic image (right) at corresponding positions to each other obtained by the aforementioned known method are displayed side by side. FIG. 22B shows an example in which a volume rendering image of a gesture region (here, large intestine) which is the display target region viewed from the outside (hereinafter, "appearance image") is generated in advance, then a real endoscope image (left) and a virtual endoscopic image (right) at corresponding positions to each other are displayed, in addition to the appearance image, and further an arrow indicating the corresponding positions is displayed in the appearance image. FIG. 22C shows an example in which a cross-sectional image representing a cross-section along the traveling direction of the endoscope is generated by the virtual endoscopic image generation unit 41 at a position corresponding to the position at which a real endoscope image has been obtained, and the generated cross-sectional image (right) and real endoscope image are displayed side by side. Note that the arrow in the cross-sectional image indicates the corresponding positions described above. FIG. 22D shows an example in which a real endoscopic image (within an inner circle) and a virtual endoscopic image (within an outer rectangle) are displayed superimposed on top of each other such that the aforementioned corresponding positions agree to each other.

As described above, in the fourth embodiment of the present invention, the medical information registration unit 51 registers a CT image, the source data for generating a virtual endoscopic image, in the medical information database 53, instead of a previously generated virtual endoscopic image, and if the CT image is selected as the display target medical information, the virtual endoscopic image generation unit 41 generates a virtual endoscopic image according to given conditions. This allows virtual endoscopic images viewed from various positions and directions to be flexibly generated and displayed.

Further, the selection of simultaneous display of real and virtual endoscopic images can be made through the endoscopic image display mode selection UI 40, so that the simultaneous display of real and virtual endoscope images at corresponding positions is possible. In this way, in the fourth embodiment of the present invention, image display more responding to the user demand is possible by displaying endoscope related medical information in more interactive fashion.

The virtual endoscopic image generation unit 41 in the fourth embodiment described above is provided in the medical information display apparatus 1, but a configuration may be adopted in which the virtual endoscopic image generation unit 41 is provided in a separate apparatus with which the medical information display apparatus 1 may communicate via the network 9 (e.g., one of the servers described above, such as the medical information management server 2 or the like, or an image processing server provided separately). Then, conditions for generating a virtual endoscopic image are transmitted to the apparatus by the medical information display apparatus 1, a virtual endoscopic image is generated by the apparatus according to the received conditions, and the generated virtual endoscopic image is returned to the medical information display apparatus 1.

Further, an arrangement may be adopted in which the virtual endoscopic image generation unit 41 is not provided, and a previously generated virtual endoscopic image is obtained as in the first to third embodiments and the obtained virtual endoscopic image is displayed simultaneously with the real endoscopic image according to the selection received by the endoscopic image display mode selection UI 40. In the case where a virtual endoscopic image at the position corresponding to the position at which the real endoscopic image has been obtained is already generated, in particular, it is more efficient to use the previously generated virtual endoscopic image.

Each embodiment described above is provided for illustrative purposes only and all the explanations above should not be used to limit the technical scope of the present invention. Further, various changes and modifications made to the system configurations, hardware configurations, processing flows, module configurations, user interfaces, specific processing contents, and the like without departing from the spirit of the present invention are included in the technical scope of the present invention.

For example, a characteristic configuration of each embodiment may be combined, as appropriate, to produce a new embodiment. More specifically, the medical information selection UI 39 of the third embodiment of the present invention may be added to the first embodiment or the endoscopic image display mode selection UI 40 and the virtual endoscopic image generation unit 41 of the fourth embodiment may be added to the first or second embodiment.

Further, the description has been made of a case in which real data of medical information are also registered in the medical information database 53 of each embodiment. But, an arrangement may be adopted in which, instead of real data of medical information, link information (address information) for gaining access to the real data is registered in the database 53 and the real data stored in a database of the source system of the real data are to be used (by setting the hyperlink destination to the database of the source system of the data), and the real data may be obtained based on the link information only when the medical information becomes the display target.

In the embodiments described above, medical information management server 2 for integrally managing medical information is provided and medical information display apparatus 1 obtains medical information from the medical information database 53 of the medical information management server 2. But an arrangement may be adopted in which medical information is obtained directly from each of other systems, such as the image diagnostic system 5, endoscopic examination system 6, and the like.

Further, the medical information display apparatus 1 may include the medical information database 53. In this case, it is only necessary to provide the function of the medical information retrieval unit 52 in the medical information obtaining unit 35 or medical information pre-obtaining unit 37.

In the embodiments described above, the description has been made of a case in which the medical information display apparatus 1 is a portable device, as illustrated in FIG. 2, but it may be a desktop device having a liquid crystal display with a touch panel and a computer body.

Further, medical information (image) displayed according to an endoscope gesture may be a moving image instead of a still image. An arrangement may be adopted in which when, for example, a change pattern of regions on a trajectory of gesture is recognized based on the reference data in FIG. 103, a real or virtual endoscopic moving image sequentially representing each region on the trajectory is obtained from the medical information database 53. Alternatively, an arrangement may be adopted in which volume data, such as CT image or the like, are obtained from the medical information database 53 and a virtual endoscopic moving image is generated in the medical information display apparatus.

Still further, an arrangement may be adopted in which when a change pattern of regions on a trajectory of gesture is recognized as described above, a real or virtual endoscopic moving image sequentially representing each region on the trajectory is obtained from the medical information database 53 and a real or virtual endoscopic image of a region desired by the user is selected through a user interface identical to that of the third embodiment (FIGS. 17A, 17B). Alternatively, an arrangement may be adopted in which CT image data are obtained, instead of a virtual endoscopic image, from the medical information database 53 as in the fourth embodiment, and a virtual endoscopic image of the region selected through the aforementioned user interface is generated based on the obtained CT image data. Further, an arrangement may be adopted in which selection between still and moving images is also made through the aforementioned user interface.

What is claimed is:

1. A medical information display apparatus, comprising:
   a display unit for displaying given information;
   a gesture input unit for detecting a gesture operation performed on a display surface of the display unit and outputting gesture information representing a plurality of positions of the detected gesture operation based on the detected gesture operation;
   a first display control unit for displaying a human body icon image representing an appearance of a human body at a predetermined display position of the display unit;
   an obtaining condition identification unit for identifying a medical information obtaining condition for obtaining medical information with respect to a subject based on gesture information outputted according to a gesture operation detected by the gesture input unit while the human body icon image is displayed and display position information of the human body icon image;
   a medical information obtaining unit for selectively obtaining medical information satisfying the identified medical information obtaining condition from a medical information storage unit storing a plurality of sets of medical information; and
   a second display control unit for displaying the obtained medical information on the display unit,
   wherein the obtaining condition identification unit includes an endoscope condition identification unit that identifies a medical information obtaining condition for obtaining medical information with respect to an actual and/or a virtual endoscopic examination of the subject when the display position information of the human body icon image and a gesture trajectory obtained from the plurality of positions in the gesture position information satisfy an endoscope gesture condition, and
   wherein the endoscope condition identification unit determines whether or not the gesture operation satisfies the endoscope gesture condition based on the display position information of the human body icon image and the gesture trajectory information obtained from the plurality of positions in the gesture position information,
   the gesture operation being determined as satisfying the endoscope gesture condition when the gesture operation satisfies at least one of the following conditions:
   i) a combination of regions of the human body icon image which correspond to a position close to a start point and a position close to an end point of the gesture trajectory of the gesture operation corresponds to a predetermined combination of regions, and
   ii) a sequence of regions of the human body icon image on which the gesture trajectory of the gesture operation has passed corresponds to a predetermined sequence of the regions.

2. The medical information display apparatus of claim 1, wherein the human body icon image is an image schematically representing an entire human body.

3. The medical information display apparatus of claim 2, wherein the human body icon image is an image in which region identification information for identifying a region of the subject is related to position information of each position of the image.

4. The medical information display apparatus of claim 1, wherein when a real endoscopic image formed through imaging with an actual endoscope and a virtual endoscopic image reconstructed from a three-dimensional medical image of the subject and representing a body cavity of the subject viewed from a given position within the body cavity are obtained by the medical information obtaining unit as medical information satisfying the medical information obtaining condition for obtaining medical information with respect to the endoscopic examination, the second display control unit is a unit that displays the real endoscopic image and virtual endoscopic image simultaneously.

5. The medical information display apparatus of claim 4, wherein:
   the apparatus further comprises a selection receiving unit for receiving, when the real endoscopic image and virtual endoscopic image are obtained by the medical information obtaining unit, selection as to whether or not to cause the second display control unit to display the real endoscopic image and virtual endoscopic image simultaneously; and
   the second display control unit is a unit that displays the real endoscope image and virtual endoscope image simultaneously when selection indicating a simultaneous display is received by the selection receiving unit.

6. The medical information display apparatus of claim 1, wherein:
   the apparatus further comprises an image processing unit for performing, when a medical image representing the subject is obtained from the medical information storage unit by the medical information obtaining unit, a predetermined image processing on the obtained medical image, as required; and
   when a three-dimensional medical image representing the subject is obtained by the medical information obtaining unit as medical information satisfying the medical information obtaining condition for obtaining medical information with respect to the virtual endoscopic examination, the image processing unit is a unit that generates a virtual endoscopic image viewed from a given position within a body cavity of the subject and representing the body cavity based on the three-dimensional medical image, and the display control unit is a unit that displays the generated virtual endoscopic image.

7. The medical information display apparatus of claim 1, wherein:
   the apparatus further comprises a second selection receiving unit for list displaying, when a plurality of sets of medical information satisfying the medical information obtaining condition is obtained by the medical information obtaining unit, the plurality of sets of medical information on the display unit and receiving selection of display target medical information; and the second display control unit is a unit that displays the medical information selected by the second selection receiving unit.

8. The medical information display apparatus of claim 7, wherein the plurality of sets of medical information satisfying the medical information obtaining condition represents examinations performed at different times.

9. The medical information display apparatus of claim 7, wherein the plurality of sets of medical information satisfying the medical information obtaining condition represents examinations of different regions of the subject.

10. The medical information display apparatus of claim 7, wherein the second selection receiving unit is a unit that, when performing the list display, displays the plurality of sets of medical information satisfying the medical information obtaining condition in the form of thumbnails or icons.

11. A medical information display system in which a medical information supply apparatus for selectively supplying medical information of a subject based on a given medical information obtaining condition and a medical information display apparatus for displaying the medical information are communicatively linked via a network, wherein the medical information display apparatus comprises:
 a display unit for displaying given information;
 a gesture input unit for detecting input of a gesture performed on a display surface of the display unit and outputting gesture position information representing a plurality of positions of the detected gesture on the display surface;
 an obtaining condition identification unit for displaying a human body icon image schematically representing an appearance of an entire human body on the display unit, causing the gesture input unit to receive gesture input while the human body icon image is displayed, and identifying a medical information obtaining condition for obtaining medical information of a subject based on gesture position information outputted according to the gesture input and a position of the human body icon image on the display surface;
 a medical information obtaining unit for obtaining medical information satisfying the identified medical information obtaining condition from the medical information supply apparatus; and
 a display control unit for displaying the obtained medical information on the display unit,
 wherein the obtaining condition identification unit includes an endoscope condition identification unit for recognizing an endoscope gesture representing an insertion path of an endoscope in the subject represented by the human body icon image when the display position information of the human body icon image and a gesture trajectory obtained from the plurality of positions in the gesture position information is recognized to satisfy an endoscope gesture condition that identifies a medical information obtaining condition for obtaining medical information of an actual and/or a virtual endoscopic examination of the subject, and
 wherein the endoscope condition identification unit determines whether or not the gesture operation satisfies the endoscope gesture condition based on the display position information of the human body icon image and the gesture trajectory information obtained from the plurality of positions in the gesture position information,
 the gesture operation being determined as satisfying the endoscope gesture condition when the gesture operation satisfies at least one of the following conditions:
  i) a combination of regions of the human body icon image which correspond to a position close to a start point and a position close to an end point of the gesture trajectory of the gesture operation corresponds to a predetermined combination of regions, and
  ii) a sequence of regions of the human body icon image on which the gesture trajectory of the gesture operation has passed corresponds to a predetermined sequence of the regions.

12. The medical information display system of claim 11, wherein the medical information supply apparatus comprises:
 a medical information storage unit storing a plurality of sets of medical information in a data structure that allows selection of medical information based on a given medical information obtaining condition;
 an obtaining condition receiving unit for receiving a medical information obtaining condition from the medical information display apparatus;
 a medical information retrieval unit for obtaining medical information satisfying the received medical information obtaining condition from the medical information storage unit; and
 a medical information transmission unit for transmitting the obtained medical information to the medical information display apparatus that has transmitted the medical information obtaining condition.

13. A medical information display method, comprising:
 a step of displaying a human body icon image schematically representing an appearance of an entire human body on a display unit;
 a step of receiving input of a gesture performed on a display surface of the display unit while the human body icon image is displayed and outputting gesture position information representing a position of the inputted gesture on the display surface;
 a step of identifying a medical information obtaining condition for obtaining medical information of a subject based on the outputted gesture position information and a position of the human body icon image on the display surface;
 a step of selectively obtaining medical information satisfying the identified medical information obtaining condition from a medical information storage unit storing a plurality of sets of medical information; and
 a step of displaying the obtained medical information,
 wherein the step of identifying medical information obtaining condition includes a step of recognizing an endoscope gesture representing an insertion path of an endoscope in the subject represented by the human body icon image when the display position information of the human body icon image and a gesture trajectory obtained from the plurality of positions in the gesture position information is recognized to satisfy an endoscope gesture condition that identifies a medical information obtaining condition for obtaining medical information of an actual and/or a virtual endoscopic examination of the subject, and
 wherein the endoscope gesture is determined as satisfying the endoscope gesture condition when the endoscope gesture satisfies at least one of the following conditions:
  i) a combination of regions of the human icon image which correspond to a position close to a start point and a position close to an end point of the gesture trajectory of the endoscope gesture corresponds to a predetermined combination of regions, and ii) a sequence of regions of the human body icon image on which the gesture trajectory of the gesture operation has passed corresponds to a predetermined sequence of the regions.

14. A non-transitory recording medium on which is recorded a medical information display control program for causing a computer to perform:
   a step of displaying a human body icon image schematically representing an appearance of an entire human body on a display unit;
   a step of receiving input of a gesture performed on a display surface of the display unit while the human body icon image is displayed and outputting gesture position information representing a position of the inputted gesture on the display surface;
   a step of identifying a medical information obtaining condition for obtaining medical information of the subject based on the outputted gesture position information and a position of the human body icon image on the display surface;
   a step of selectively obtaining medical information satisfying the identified medical information obtaining condition from a medical information storage unit storing a plurality of sets of medical information; and
   a step of displaying the obtained medical information,
   wherein, in the step of identifying medical information obtaining condition, the program causes the computer to perform a step of recognizing an endoscope gesture representing an insertion path of an endoscope in the subject represented by the human body icon image when the display position information of the human body icon image and a gesture trajectory obtained from the plurality of positions in the gesture position information is recognized to satisfy an endoscope gesture condition that identifies a medical information obtaining condition for obtaining medical information of an actual and/or a virtual endoscopic examination of the subject, and
   wherein the endoscope gesture is determined as satisfying the endoscope gesture condition when the endoscope gesture satisfies at least one of the following conditions:
      i) a combination of regions of the human icon image which correspond to a position close to a start point and a position close to an end point of the gesture trajectory of the endoscope gesture corresponds to a predetermined combination of regions, and
      ii) a sequence of regions of the human body icon image on which the gesture trajectory of the gesture operation has passed corresponds to a predetermined sequence of the regions.

15. A medical information display apparatus, comprising:
   a display unit for displaying given information;
   a gesture input unit for detecting a gesture operation performed on a display surface of the display unit and outputting gesture information representing a plurality of positions of the detected gesture operation based on the detected gesture operation;
   a first display control unit for displaying a human body icon image representing an appearance of a human body at a predetermined display position of the display unit;
   an obtaining condition identification unit for identifying a medical information obtaining condition for obtaining medical information with respect to a subject based on gesture information outputted according to a gesture operation detected by the gesture input unit while the human body icon image is displayed and display position information of the human body icon image;
   a medical information obtaining unit for selectively obtaining medical information satisfying the identified medical information obtaining condition from a medical information storage unit storing a plurality of sets of medical information; and
   a second display control unit for displaying the obtained medical information on the display unit,
   wherein the obtaining condition identification unit includes an endoscope condition identification unit that identifies a medical information obtaining condition for obtaining medical information with respect to an actual and/or a virtual endoscopic examination of the subject when the display position information of the human body icon image and a gesture trajectory obtained from the plurality of positions in the gesture information satisfy an endoscope gesture condition, and
   wherein the endoscope condition identification unit determines whether or not the gesture operation satisfies the endoscope gesture condition based on the display position information of the human body icon image and the gesture trajectory information obtained from the plurality of positions in the gesture position information,
   the gesture operation being determined as satisfying the endoscope gesture condition when the gesture operation satisfies at least one of the following conditions:
      i) a shape of the trajectory of the gesture operation is a predetermined shape and the end point of the trajectory of the gesture operation is on a predetermined region of the human body icon image, and
      ii) a shape of the trajectory of the gesture operation is a predetermined shape and positions of the trajectory of the gesture operation are over predetermined regions of the human body icon image.

16. A medical information display method, comprising:
   a step of displaying a human body icon image schematically representing an appearance of an entire human body on a display unit;
   a step of receiving input of a gesture performed on a display surface of the display unit while the human body icon image is displayed and outputting gesture position information representing a position of the inputted gesture on the display surface;
   a step of identifying a medical information obtaining condition for obtaining medical information of a subject based on the outputted gesture position information and a position of the human body icon image on the display surface;
   a step of selectively obtaining medical information satisfying the identified medical information obtaining condition from a medical information storage unit storing a plurality of sets of medical information; and
   a step of displaying the obtained medical information,
   wherein the step of identifying medical information obtaining condition includes a step of recognizing an endoscope gesture representing an insertion path of an endoscope in the subject represented by the human body icon image when the display position information of the human body icon image and a gesture trajectory obtained from the plurality of positions in the gesture position information is recognized to satisfy an endoscope gesture condition that identifies a medical information obtaining condition for obtaining medical information of an actual and/or a virtual endoscopic examination of the subject, and
   wherein the endoscope gesture is determined as satisfying the endoscope gesture condition when the endoscope gesture satisfies at least one of the following conditions:

i) a shape of the trajectory of the endoscope gesture is a predetermined shape and the end point of the trajectory of the endoscope gesture is on a predetermined region of the human body icon image, and
ii) a shape of the trajectory of the endoscope gesture is a predetermined shape and positions of the trajectory of the endoscope gesture are over predetermined regions of the human body icon image.

17. A non-transitory recording medium on which is recorded a medical information display control program for causing a computer to perform:
   a step of displaying a human body icon image schematically representing an appearance of an entire human body on a display unit;
   a step of receiving input of a gesture performed on a display surface of the display unit while the human body icon image is displayed and outputting gesture position information representing a position of the inputted gesture on the display surface;
   a step of identifying a medical information obtaining condition for obtaining medical information of the subject based on the outputted gesture position information and a position of the human body icon image on the display surface;
   a step of selectively obtaining medical information satisfying the identified medical information obtaining condition from a medical information storage unit storing a plurality of sets of medical information; and
   a step of displaying the obtained medical information,
   wherein, in the step of identifying medical information obtaining condition, the program causes the computer to perform a step of recognizing an endoscope gesture representing an insertion path of an endoscope in the subject represented by the human body icon image when the display position information of the human body icon image and a gesture trajectory obtained from the plurality of positions in the gesture position information is recognized to satisfy an endoscope gesture condition that identifies a medical information obtaining condition for obtaining medical information of an actual and/or a virtual endoscopic examination of the subject, and
   wherein the endoscope gesture is determined as satisfying the endoscope gesture condition when the endoscope gesture satisfies at least one of the following conditions:
   i) a shape of the trajectory of the endoscope gesture is a predetermined shape and the end point of the trajectory of the endoscope gesture is on a predetermined region of the human body icon image, and
   ii) a shape of the trajectory of the endoscope gesture is a predetermined shape and positions of the trajectory of the endoscope gesture are over predetermined regions of the human body icon image.

* * * * *